United States Patent
Vargas-Inchaustegui et al.

(10) Patent No.: US 12,163,153 B2
(45) Date of Patent: Dec. 10, 2024

(54) METHODS OF MANUFACTURING ALLOGENEIC CAR T CELLS

(71) Applicant: ALLOGENE THERAPEUTICS, INC., South San Francisco, CA (US)

(72) Inventors: Diego A. Vargas-Inchaustegui, Belmont, CA (US); Thomas Charles Pertel, San Mateo, CA (US); Barbra Johnson Sasu, San Francisco, CA (US)

(73) Assignee: Allogene Therapeutics, Inc., South San Francisco, CA (US)

( * ) Notice: Subject to any disclaimer, the term of this patent is extended or adjusted under 35 U.S.C. 154(b) by 680 days.

(21) Appl. No.: 16/857,394

(22) Filed: Apr. 24, 2020

(65) Prior Publication Data

US 2020/0339944 A1 Oct. 29, 2020

Related U.S. Application Data

(60) Provisional application No. 62/839,449, filed on Apr. 26, 2019.

(51) Int. Cl.
*C12N 5/00* (2006.01)
*A61K 35/17* (2015.01)
*C12N 5/0783* (2010.01)

(52) U.S. Cl.
CPC ............ *C12N 5/0018* (2013.01); *A61K 35/17* (2013.01); *C12N 5/0636* (2013.01); *C12N 2500/05* (2013.01); *C12N 2501/2307* (2013.01); *C12N 2501/2315* (2013.01); *C12N 2510/00* (2013.01)

(58) Field of Classification Search
CPC .................. A61K 35/17; C12N 5/0636; C12N 2501/2307; C12N 2501/2315
See application file for complete search history.

(56) References Cited

U.S. PATENT DOCUMENTS

| | | |
|---|---|---|
| 4,816,567 A | 3/1989 | Cabilly et al. |
| 4,975,278 A | 12/1990 | Senter et al. |
| 5,571,894 A | 11/1996 | Wels et al. |
| 5,587,458 A | 12/1996 | King et al. |
| 5,770,429 A | 6/1998 | Lonberg |
| 5,821,337 A | 10/1998 | Carter et al. |
| 5,827,642 A | 10/1998 | Ridell et al. |
| 5,869,046 A | 2/1999 | Presta et al. |
| 6,040,177 A | 3/2000 | Ridell et al. |
| 6,075,181 A | 6/2000 | Kucherlapati et al. |
| 6,150,584 A | 11/2000 | Kucherlapati |
| 6,248,516 B1 | 6/2001 | Winter et al. |
| 6,319,494 B1 | 11/2001 | Capon et al. |
| 6,797,514 B2 | 9/2004 | Brenson et al. |
| 6,867,041 B2 | 3/2005 | Berenson et al. |
| 6,905,874 B2 | 6/2005 | Berenson et al. |
| 6,982,321 B2 | 1/2006 | Winter et al. |
| 7,041,870 B2 | 5/2006 | Tomizuka et al. |
| 7,087,409 B2 | 8/2006 | Barbas et al. |
| 7,189,826 B2 | 3/2007 | Rodman |
| 7,527,791 B2 | 5/2009 | Adams et al. |
| 7,741,465 B1 | 6/2010 | Eshhar et al. |
| 8,486,693 B2 | 7/2013 | Park et al. |
| 8,999,715 B2 | 4/2015 | Bonini et al. |
| 9,428,727 B2 | 8/2016 | Leist et al. |
| 9,974,808 B2 | 5/2018 | Bonini et al. |
| 10,000,736 B2 | 6/2018 | Karlsson-Parra et al. |
| 10,233,425 B2 | 3/2019 | Powell |
| 11,395,835 B2 | 7/2022 | Bonini et al. |
| 2007/0061900 A1 | 3/2007 | Murphy et al. |
| 2010/0035282 A1 | 2/2010 | Bonini et al. |
| 2011/0286980 A1 | 11/2011 | Brenner |
| 2012/0130076 A1 | 5/2012 | Holt et al. |
| 2014/0171649 A1 | 6/2014 | Li et al. |
| 2014/0286987 A1 | 9/2014 | Spencer et al. |
| 2015/0266973 A1 | 9/2015 | Jarjour et al. |
| 2016/0009813 A1 | 1/2016 | Themeli et al. |
| 2016/0046700 A1 | 2/2016 | Foster et al. |
| 2016/0137980 A1 | 5/2016 | Abbot et al. |
| 2017/0274014 A1 | 9/2017 | Brogdon |
| 2017/0355957 A1 | 12/2017 | Biondi et al. |
| 2018/0156800 A1* | 6/2018 | Lin ...................... G01N 33/505 |
| 2018/0207272 A1* | 7/2018 | Reisner ................ C12N 5/0648 |
| 2018/0318349 A1 | 11/2018 | Thompson et al. |
| 2019/0119658 A1 | 4/2019 | Ostertag et al. |

FOREIGN PATENT DOCUMENTS

| | | | |
|---|---|---|---|
| RU | 2015128276 A | 1/2017 | |
| WO | 9301161 A1 | 1/1993 | |
| WO | WO-2011057124 A1 * | 5/2011 | ............. A61K 35/17 |
| WO | 2012079000 A1 | 6/2012 | |
| WO | 2012129514 A1 | 9/2012 | |
| WO | 2013153391 A1 | 10/2013 | |

(Continued)

OTHER PUBLICATIONS

Plum et al., J Immunol., 1993, 150(7): 2706-2716.*
Junger et al., Circulatory Shock, 1994, 42:190-196.*
Almagro, et al., "Humanization of antibodies", Frontiers in Bioscience, vol. 13, pp. 1619-1633, (2008).
Boerner, P, et al., "Production of Antigen-Specific Human Monoclonal Antibodies From in Vitro-Primed Human Splenocytes", J Immunol 1991; 147:86-95; http://www.jimmunol.org/content/147/1/86.
Brinkmann, Ulrich, et al., "The making of bispecific antibodies", MABS, 2017, vol. 9, No. 2, 182-212.
Brodeur, Bernart R., et al., "Mouse-Human Myeloma Partners for the production of Heterohybridomas", Monoclonal Antibody Production Techniques and Applications, pp. 51-56, 3Mercel Dekker Inc, (1987).

(Continued)

*Primary Examiner* — Hong Sang
(74) *Attorney, Agent, or Firm* — Allogene Therapeutics, Inc.

(57) ABSTRACT

Described herein are improved media for culturing immune cells, and methods of use thereof. In particular, cell growth media described herein are particularly suitable for T-cell expansion, which can be used for manufacture of cells useful in adoptive cell therapies, including therapies using chimeric antigen receptors (e.g., CAR-T cell therapy).

18 Claims, 4 Drawing Sheets

Specification includes a Sequence Listing.

(56) References Cited

FOREIGN PATENT DOCUMENTS

| WO | 2014127261 | A1 | | 8/2014 | | |
|---|---|---|---|---|---|---|
| WO | 2015090229 | A1 | | 6/2015 | | |
| WO | 2016/109410 | A2 | | 7/2016 | | |
| WO | WO-2016191315 | A1 | * | 12/2016 | ............. | A61K 35/17 |
| WO | 2017/009853 | A1 | | 1/2017 | | |
| WO | 2017/015427 | A1 | | 1/2017 | | |
| WO | 2017070395 | A1 | | 4/2017 | | |
| WO | 2017099712 | A1 | | 6/2017 | | |
| WO | 2017114497 | A1 | | 7/2017 | | |
| WO | 2017127755 | A1 | | 7/2017 | | |
| WO | WO-2017117418 | A1 | * | 7/2017 | ............. | A61K 35/17 |
| WO | WO2018064681 | A1 | | 4/2018 | | |
| WO | 2018102761 | A1 | | 6/2018 | | |
| WO | WO-2019089855 | A1 | * | 5/2019 | ............. | A61K 35/17 |
| WO | WO-2019209715 | A1 | * | 10/2019 | ........... | A61K 31/194 |
| WO | WO2020051374 | A1 | | 3/2020 | | |

OTHER PUBLICATIONS

Courtois, Anthony, et al., "Complement dependent cytotoxicity activity of therapeutic antibody fragments is acquired by immunogenic glycan coupling", Research Article, Biotechnology of Human Disorders, Electronic Journal of Biotechnology, vol. 15 No. 5, Issue of Sep. 15, 2012.

Dall'Acqua, William F., et al., "Antibody humanization by framework shuffling", Methods; 2005 36(1):43-60; DOI; 10.1016/j.ymeth.2005.01.005.

Eli, Robert, et al., "Ionic immune suppression within the tumour microenvironment limits T cell effector function", Nature. Sep. 22, 2016; 537(7621): 539-543. doi:10.1038/nature19364.

Finney, Helen, et al., "Chimeric Receptors Providing Both Primary and Costimulatory Signaling in T Cells from a Single Gene Product", J Immunol Sep. 15, 1998, 161 (6) 2791-2797.

Gross, Gideon, et al., "Therapeutic Potential of T Cell Chimeric Antigen Receptors (CARs) in Cancer Treatment: Counteracting Off-Tumor Toxicities for Safe CAR T Cell Therapy", Annual Review of Pharmacology and Toxicology; vol. 56:59-83 (Volume publication date Jan. 2016) https://doi.org/10.1146/annurev-pharmtox-010814-124844.

Holliger, Philipp, et al., ""Diabodies": Small bivalent and bispecific antibody fragments", Proc. Natl. Acad. Sci. USA, vol. 90, pp. 6444-6448, Jul. 1993, Biophysics.

Hudson, Peter J., et al., "Engineered antibodies", Review, National Medicine, vol. 9, No. 1, (2003).

Kalos, Michael, et al., "T Cells with Chimeric Antigen Receptors Have Potent Antitumor Effects and Can Establish Memory in Patients with Advanced Leukemia", Science Transnational Medicine, vol. 3 Issue 95 95ra73, 2011.

Kashmiri, Syed V.S., et al., "SDR grafting—a new approach to antibody humanization", Methods, vol. 36, pp. 25-34, (2005).

Klimka, A., et al., "Human anti-CD30 recombinant antibodies by guided phage antibody selection using cell panning", British Journal of Cancer, vol. 83, No. 2, pp. 252-260, (2000).

Kozbor, Danuta, et al., "A Human Hybrid Myeloma for Production of Human Monoclonal Antibodies", The Journal of Immunology, vol. 133, No. 6 (1984).

Krause, Anja, et al., "Antigen-dependent CD28 Signaling Selectively Enhances Survival and Proliferation in Genetically Modified Activated Human Primary T Lymphocytes", The Journal of experimental medicine vol. 188,4 (1998): 619-26. doi:10.1084/jem.188.4.619.

Li, Jian, et al., "Human antibodies for immunotherapy development generated via a human B cell hybridoma technology", PNAS, 2006 vol. 103, No. 10, pp. 3557-3562.

Lonberg, Nils, "Fully human antibodies from transgenic mouse and phage display platforms", Current Opinion in Immunology, 2008, 20:450-459.

Lonberg, Nils, "Human antibodies from transgenic animals", Review, Nature Biotechnology, vol. 23, No. 9, pp. 1117-1125 (2005).

Morrison, Sherie L., et al., "Chimeric human antibody molecules: Mouse antigen-binding domains with human constant region domains", Proc. Natl. Acad. Sci., USA, vol. 81, pp. 6851-6855, (1984).

Muller, Dafne, et al., "Bispecific Antibodies for Cancer Immunotherapy", Review Article, Biodrugs 2010; 24 (2):89-98.

Ni, Jian, "Research Progress and Prospect of Antibodomics and Antibodomics-based Drugs", Xiandai Mianyixue; 2006, vol. 26, No. 4; pp. 265-268; (EN translation).

Niculescu-Duvaz, I., et al., "Antibody-directed enzyme prodrug therapy (ADEPT): a review", Advanced Drug Delivery Reviews 26 (1997) 151-172.

Osbourn, Jane, et al., "From rodent reagents to human therapeutics using antibody guided selection", Methods, vol. 36, pp. 61-68, (2005).

Padlan, Eduardo A., et al., "A Possible Procedure for Reducing the Immunogenicity of Antibody Variable Domains While Preserving Their Ligand-Binding Properties", Mol. Immunol, vol. 28, pp. 489-498, (1991).

Payne, Gillian, "Progress in immunoconjugate cancer therapeutics", Pipeline, Cancer Cell, vol. 3, pp. 207-212, (2003).

Pluckthun, A., "Antibodies from *Escherichia Coli*", The Pharmacology of Monoclonal Antibodies, Chapter 11, pp. 269-315 (1994).

Porter, David L., et al., "Chimeric Antigen Receptor-Modified T Cells in Chronic Lymphoid Leukemia", N Engl J Med 2011;365:725-33.

Presta, L. G., et al., "Humanization of an antibody directed against IgE.", J Immunol 1993; 151:2623-2632.

Queen, Cary, et al., "A humanized antibody that binds to the interleukin 2 receptor", Proc. Natl. Acad. Sci. USA, vol. 86, pp. 10029-10033, (1989).

Riechmann, Lutz, et al., "Reshaping human antibodies for therapy", Nature, vol. 332, pp. 323-327, (1988).

Rosok, Mae Joanne, et al., "A Combinatorial Library Strategy for the Rapid Humanization of Anticarcinoma BR96 Fab", The Journal of Biological Chemistry, vol. 271, No. 37, Issue of Sep. 13, pp. 22611-22618, 1996.

Sims, M. J., et al., "A humanized CD18 antibody can block function without cell destruction", J Immunol 1993; 151:2296-2308.

Song, De-Gang, et al., "CD27 costimulation augments the survival and antitumor activity of redirected human T cells in vivo", Blood (2012) 119 (3): 696-706.

Stockmeyer, Bernhard, et al., "Triggering FCa-Receptor I (CD89) Recruits Neutrophils as Effector Cells for CD20-Directed Antibody Therapy", J Immunol 2000; 165:5954-5961.

Syrigos, Konstantinos, et al., "Antibody Directed Enzyme Prodrug Therapy (ADEPT): A Review of the Experimental and Clinical Considerations", Review, Anticancer Research 19: 605-614 (1999).

Van Dijk, Marc A., et al., "Human antibodies as next generation therapeutics", Curr Opin Chem Biol, vol. 5, No. 4, pp. 368-374, (2001).

Vollmers, H. P., et al., "Death by Stress: Natural IgM-Induced Apoptosis", Methods Find Exp Clin Pharmacol 2005, 27(3): 185-191.

Vollmers, H. P., et al., "The "early birds": natural IgM antibodies and immune surveillance", Review, Histol Histopathol (2005) 20: 927-937.

Xu, Yang, "Closely related T-memory stem cells correlate with in vivo expansion of CAR.CD19-T cells and are preserved by IL-7 and IL-15", Blood. Jun. 12, 2014; 123(24): 3750-3759.

Xu, Xiao-Jun, et al., "Multiparameter comparative analysis reveals differential impacts of various cytokines on CART cell phenotype and function ex vivo and in vivo", Oncotarget, 2016, vol. 7, (No. 50), pp. 82354-82368.

Brenner, Malcom K., et al., "Adoptive T Cell Therapy of Cancer", Curr Opin Immunol. Apr. 2010; 22(2): 251-257. doi:10.1016/j.coi.2010.01.020.

EPO, "International Search Report & Written Opinion", mailed on Jun. 19, 2020 for International Application No. PCT/2020/029722.

Eshhar, Zelig, et al., "Specific activation and targeting of cytotoxic lymphocytes through chimeric single chains consisting of antibody-

(56) References Cited

OTHER PUBLICATIONS binding domains and the gamma or zeta subunits of the immunoglobulin and T-cell receptors.", Immunology; Proc Natl Acad Sci U S A. Jan. 15, 1993; 90(2): 720-724.

Rosenberg, Steven A., et al., "Adoptive cell transfer: a clinical path to effective cancer immunotherapy", Nat Rev Cancer. Apr. 2008 ; 8(4): 299-308. doi:10.1038/nrc2355.

Sadelain, Michel, et al., "The promise and potential pitfalls of chimeric antigen receptors", Current Opinion in Immunology 2009, 21:215-223.

Baca, Manuel, et al., "Antibody Humanization Using Monovalent Phage Display", The Journal of Biological Chemistry, vol. 272, No. 16, Issue of Apr. 18, pp. 10678-10684, 1997.

Carter, Robert H., et al., "CD19: Lowering the Threshold for Antigen Receptor Stimulation of B Lymphocytes", Reports, Science, vol. 256 pp. 105-107; Apr. 3, 1992.

Eil, Robert, et al., "Elevated potassium levels suppress T cell activation within tumors", Eil et al. Journal for Immuno Therapy of Cancer 2015, 3(Suppl 2):P403; http://www.immunotherapyofcancer.org/content/3/S2/P403.

Eil, Robert, et al., "Ionic immune suppression within the tumour microenvironment limits T cell effector function", Nature, Sep. 22, 2016; 537(7621): 539-543. doi:10.1038/nature19364.

Genbank, accession No. NP_006130.1, T-cell-specific surface glycoprotein CD28 isoform 1 precursor, *homo sapience*, total 4 pages. Aug. 14, 2022.

Genbank, "*Homo sapiens* CD28 molecule (CD28), transcript variant 1, mRNA", NCBI Reference Sequence: NM_006139.4; Aug. 14, 2022.

Gurusamy, Devikala, et al., "Novel 'elements' of immune suppression within the tumor microenvironment", Cancer Immunol Res. Jun. 2017 ; 5(6): 426-433. doi:10.1158/2326-6066.CIR-17-0117.

\* cited by examiner

SEQUENCE LISTING

```
<160> NUMBER OF SEQ ID NOS: 26

<210> SEQ ID NO 1
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

Cys Pro Tyr Ser Asn Pro Ser Leu Cys Ser Gly Gly Gly Gly Ser Glu
1               5                   10                  15

Leu Pro Thr Gln Gly Thr Phe Ser Asn Val Ser Thr Asn Val Ser Pro
                20                  25                  30

Ala Lys Pro Thr Thr Thr Ala Cys Pro Tyr Ser Asn Pro Ser Leu Cys
            35                  40                  45

Ser Gly Gly Gly Gly Ser Pro Ala Pro Arg Pro Pro Thr Pro Ala Pro
        50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

```
Ile Tyr Ile Trp Ala Pro Leu Ala Gly Thr Cys Gly Val Leu Leu Leu
            100                 105                 110
Ser Leu Val Ile Thr Leu Tyr Cys Asn His Arg Asn Arg Arg Val
        115                 120                 125
Cys Lys Cys Pro Arg Pro Val Val
    130                 135

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Gly Thr Ser Leu Leu Cys Trp Met Ala Leu Cys Leu Leu Gly Ala
1               5                   10                  15
Asp His Ala Asp Ala
            20

<210> SEQ ID NO 3
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly Thr Ser Leu Leu Cys Trp Met Ala Leu Cys Leu Leu Gly Ala
1               5                   10                  15
Asp His Ala Asp Ala Cys Pro Tyr Ser Asn Pro Ser Leu Cys Ser Gly
            20                  25                  30
Gly Gly Gly Ser Glu Leu Pro Thr Gln Gly Thr Phe Ser Asn Val Ser
        35                  40                  45
Thr Asn Val Ser Pro Ala Lys Pro Thr Thr Thr Ala Cys Pro Tyr Ser
50                  55                  60
Asn Pro Ser Leu Cys Ser Gly Gly Gly Ser Pro Ala Pro Arg Pro
65                  70                  75                  80
Pro Thr Pro Ala Pro Thr Ile Ala Ser Gln Pro Leu Ser Leu Arg Pro
                85                  90                  95
Glu Ala Cys Arg Pro Ala Ala Gly Gly Ala Val His Thr Arg Gly Leu
            100                 105                 110
Asp Phe Ala Cys Asp Ile Tyr Ile Trp Ala Pro Leu Ala Gly Thr Cys
        115                 120                 125
Gly Val Leu Leu Leu Ser Leu Val Ile Thr Leu Tyr Cys Asn His Arg
    130                 135                 140
Asn Arg Arg Arg Val Cys Lys Cys Pro Arg Pro Val Val
145                 150                 155

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

```
Cys Pro Tyr Ser Asn Pro Ser Leu Cys
1               5
```

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Asn Ser Glu Leu Leu Ser Leu Ile Asn Asp Met Pro Ile Thr Asn Asp
1               5                   10                  15

Gln Lys Lys Leu Met Ser Asn Asn
            20
```

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Cys Gln Phe Asp Leu Ser Thr Arg Arg Leu Lys Cys
1               5                   10
```

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Cys Gln Tyr Asn Leu Ser Ser Arg Ala Leu Lys Cys
1               5                   10
```

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Cys Val Trp Gln Arg Trp Gln Lys Ser Tyr Val Cys
1               5                   10
```

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Cys Met Trp Asp Arg Phe Ser Arg Trp Tyr Lys Cys
1               5                   10
```

<210> SEQ ID NO 10
<211> LENGTH: 25

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Phe Val Leu Asn Trp Tyr Arg Met Ser Pro Ser Asn Gln Thr Asp
1               5                   10                  15

Lys Leu Ala Ala Phe Pro Glu Asp Arg
            20                  25

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gly Thr Tyr Leu Cys Gly Ala Ile Ser Leu Ala Pro Lys Ala Gln
1               5                   10                  15

Ile Lys Glu

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Leu Pro Thr Gln Gly Thr Phe Ser Asn Val Ser Thr Asn Val Ser
1               5                   10                  15

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gln Asn Asp Thr Ser Gln Thr Ser Ser Pro Ser
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Leu Ala Val Ser Thr Ile Ser Ser Phe Phe Pro Pro Gly Tyr Gln
1               5                   10                  15

<210> SEQ ID NO 15
<211> LENGTH: 45
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 15

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 16
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Ile Tyr Ile Trp Ala Pro Leu Ala Gly Thr Cys Gly Val Leu Leu Leu
1               5                  10                 15

Ser Leu Val Ile Thr
            20
```

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Phe Trp Val Leu Val Val Gly Gly Val Leu Ala Cys Tyr Ser Leu
1               5                  10                 15

Leu Val Thr Val Ala Phe Ile Ile Phe Trp Val
            20                  25
```

<210> SEQ ID NO 19
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
                35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 20
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40
```

```
<210> SEQ ID NO 21
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
aagcgcggca ggaagaagct cctctacatt tttaagcagc cttttatgag gcccgtacag    60
acaacacagg aggaagatgg ctgtagctgc agatttcccg aggaggagga aggtgggtgc   120
gagctg                                                              126

<210> SEQ ID NO 22
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
agatccaaaa gaagccgcct gctccatagc gattacatga atatgactcc acgccgccct    60
ggccccacaa ggaaacacta ccagccttac gcaccaccta gagatttcgc tgcctatcgg   120
agc                                                                 123

<210> SEQ ID NO 23
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 24
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
agggtgaagt tttccagatc tgcagatgca ccagcgtatc agcagggcca gaaccaactg    60
tataacgagc tcaacctggg acgcagggaa gagtatgacg tttgtgacaa gcgcagagga   120
cgggaccctg agatgggtgg caaaccaaga cgaaaaaacc cccaggaggg tctctataat   180
gagctgcaga aggataagat ggctgaagcc tattctgaaa taggcatgaa aggagagcgg   240
agaaggggaa aagggcacga cggtttgtac cagggactca gcactgctac gaaggatact   300
tatgacgctc tccacatgca agccctgcca cctagg                             336

<210> SEQ ID NO 25
<211> LENGTH: 24
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Leu Pro Thr Gln Gly Thr Phe Ser Asn Val Ser Thr Asn Val Ser
1               5                   10                  15

Pro Ala Lys Pro Thr Thr Thr Ala
            20

<210> SEQ ID NO 26
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Leu Arg Val Lys Phe Ser Arg Ser Ala Asp Ala Pro Ala Tyr Lys Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

US 12,163,153 B2

METHODS OF MANUFACTURING ALLOGENEIC CAR T CELLS

CROSS REFERENCE

The present application claims the benefit of priority to U.S. Provisional Application No. 62/839,449, filed on Apr. 26, 2019, the content of which is hereby incorporated by reference in its entirety.

TECHNICAL FIELD

This instant disclosure relates to cell growth media and methods for the manufacture of engineered immune cells, including those comprising chimeric antigen receptors (CARs) and engineered T cell receptors (TCRs), and methods of treating a cancer in a patient using the same.

SEQUENCE LISTING

This application contains a Sequence Listing which has been submitted electronically in ASCII format and is hereby incorporated by reference in its entirety. Said ASCII copy, created on Apr. 17, 2020, is named AT-025_02US_ST25.txt and is 14,833 bytes in size.

BACKGROUND

Adoptive transfer of immune cells genetically modified to recognize malignancy-associated antigens is showing promise as a new approach to treating cancer (see, e.g., Brenner et al., Current Opinion in Immunology, 22(2): 251-257 (2010); Rosenberg et al., Nature Reviews Cancer, 8(4): 299-308 (2008)). Immune cells can be genetically modified to express chimeric antigen receptors (CARs) (see, e.g., Eshhar et al., Proc. Natl. Acad. Sci. USA, 90(2): 720-724 (1993), and Sadelain et al., Curr. Opin. Immunol, 21(2): 215-223 (2009)). Immune cells that contain CARs, e.g. CAR-T cells (CAR-Ts), are engineered to endow them with antigen specificity while retaining or enhancing their ability to recognize and kill a target cell. Effective immune cell growth media and methods of use thereof can be particularly useful for the manufacture of engineered immune cells such as CAR-Ts. Provided herein are cell growth media and methods of manufacture addressing this need.

SUMMARY

Described herein are improved media for culturing immune cells, and methods of use. For example, described herein are media that are particularly suitable for T-cell expansion, which can be used for manufacture of cells useful in adoptive cell therapies, including therapies using chimeric antigen receptors (e.g., CAR-T cell therapy).

In one aspect, the disclosure provides a cell growth medium for T cell expansion comprising: a first stimulant and a second stimulant of cell proliferation, each independently selected from the group consisting of IL-4, IL-7, IL-10, IL-12, and IL-15, and wherein the first stimulant and the second stimulant are present in a concentration ratio of about 1000:1 to about 4:1.

In one aspect, the disclosure provides a cell growth medium for T cell expansion comprising an extracellular of modulator of cell metabolism that is extracellular potassium in a concentration of about 4 mM to about 40 mM.

In one aspect, the disclosure provides a cell growth medium for T cell expansion comprising: a first stimulant and a second stimulant of cell proliferation, each independently selected from the group consisting of IL-4, IL-7, IL-10, IL-12, and IL-15; and an extracellular of modulator of cell metabolism that is extracellular potassium in a concentration of about 4 mM to about 40 mM; and wherein the first stimulant and the second stimulant are present in a concentration ratio of about 1000:1 to about 4:1.

In some embodiments, the first stimulant of cell proliferation is IL 7.

In some embodiments, the second stimulant of cell proliferation is IL 15.

In some embodiments, the first stimulant and the second stimulant are present in a concentration ratio of about 500:1 to about 10:1, about 250:1 to about 10:1, about 200:1 to about 10:1, about 150:1 to about 10:1, about 100:1 to about 10:1, about 500:1 to about 50:1, about 250:1 to about 50:1, about 200:1 to about 50:1, about 150:1 to about 50:1, about 100:1 to about 50:1, about 500:1 to about 75:1, about 250:1 to about 75:1, about 200:1 to about 75:1, about 150:1 to about 75:1, about 100:1 to about 75:1, about 10:1 to about 4:1, about 8:1 to about 4:1, or about 7:1 to about 6:1.

In some embodiments, the first stimulant and the second stimulant are present in a concentration ratio of about 150:1, about 140:1, about 130:1, about 120:1, about 110:1, about 100:1, about 90:1, about 80:1 or about 70:1.

In some embodiments, a first stimulant is IL-7, present in a concentration of about 100 IU/mL to about 5,000 IU/mL; and a second stimulant is IL-15, present in a concentration of about 1 IU/mL to about 100 IU/mL.

In some embodiments, IL-7 is present in a concentration of about 300 IU/mL to about 5000 IU/mL, and IL-15 is present in a concentration that is about 25 IU/mL to about 50 IU/mL.

In some embodiments, IL-7 is present in a concentration of about 5000 IU/mL, and IL-15 is present in a concentration that is about 50 IU/mL.

In some embodiments, the first stimulant and the second stimulant are added to the cell culture simultaneously or sequentially.

In some embodiments, extracellular potassium is present in a concentration of about 4 mM to about 40 mM; about 10 mM to about 35 mM; about 10 mM to about 25 mM; about 20 mM to about 35 mM; about 20 mM to about 25 mM; or about 20 mM to about 30 mM.

In some embodiments, extracellular potassium is present in a concentration of about 20 mM or about 25 mM.

In some embodiments, extracellular potassium is present in a concentration less than 40 mM and more than 4 mM; less than 40 mM and more than 10 mM; less than 40 mM and more than 20 mM; or less than 40 mM and equal or more than 25 mM.

In some embodiments, extracellular potassium is present as KCl.

In some embodiments, the obtained population of T cells is enriched in $T_{CM}$ and/or $T_{SCM}$ cells.

In another aspect, the disclosure provides a method of obtaining a population of T cells in vitro, comprising culturing an initial population of T cells with a cell growth medium comprising a first stimulant and a second stimulant of cell proliferation, each independently selected from the group consisting of IL-4, IL-7, IL-10, IL-12, and IL 15; and an extracellular of modulator of cell metabolism that is extracellular potassium in a concentration of about 4 mM to about 40 mM; and wherein the first stimulant and the second stimulant are present in a concentration ratio of about 1000:1 to about 4:1, and wherein the obtained population of T cells is enriched in $T_{CM}$ and/or $T_{SCM}$ cells.

In some embodiments, the cell growth medium is the cell growth medium as described above.

In some embodiments, the obtained population of T cells comprises at least about 30%, 35%, 40%, or 45% $T_{SCM}$ cells.

In some embodiments, the obtained population of T cells comprises at least about 40% $T_{SCM}$ cells.

In some embodiments, the obtained population of T cells is about 100- to about 1000-fold that of the initial population of T cells as measured over a period of about 7-16 days.

In some embodiments, the obtained population of T cells is about 100- to about 1000-fold that of the initial population of T cells as measured over a period of about 10-14 days.

In some embodiments, obtained population of T cells is at least about 100- or about 200-fold that of the initial population of T cells.

In some embodiments, the obtained population of T cells is about 100- to about 1000-fold enriched in $T_{CM}$ and/or $T_{SCM}$ than $T_{CM}$ and/or $T_{SCM}$ of the initial population of T cells, as measured over a period of about 7-16 days.

In some embodiments, the obtained population of T cells is about 100- to about 1000-fold enriched in $T_{CM}$ and/or $T_{SCM}$ than $T_{CM}$ and/or $T_{SCM}$ of the initial population of T cells, as measured over a period of about 10-14 days.

In some embodiments, obtained population of T cells is at least about 100- or at least about 200-fold enriched in $T_{CM}$ and/or $T_{SCM}$ than $T_{CM}$ and/or $T_{SCM}$ of the initial population of T cells.

In some embodiments, the initial population of T cells is a population of engineered T cells.

In some embodiments, the initial population of T cells is a population of T cells expressing one or more chimeric antigen receptors.

In some embodiments, the T cells are allogeneic T cells.

In some embodiments, the T cells are autologous T cells.

In one aspect, the disclosure provides a population of engineered immune cells, wherein said population comprises T cells expressing one or more chimeric antigen receptors (CAR T cells), and wherein said CAR T cells are obtained using the cell growth medium as described above.

In one aspect, the disclosure provides a population of engineered immune cells, wherein said population comprises T cells expressing one or more chimeric antigen receptors (CAR T cells), and wherein said (CAR T cells) are obtained using the method as described above.

In some embodiments, the CAR T cells comprise at least about 30%, 35%, 40%, or 45% $T_{SCM}$ cells.

In some embodiments, the CAR T cells comprise at least about 40% $T_{SCM}$ cells.

In one aspect, the disclosure provides a pharmaceutical composition comprising the population of engineered immune cells as described above.

In one aspect, the disclosure provides a method of treating a disease or disorder in a subject in need thereof comprising administering to the subject the engineered immune cell of as described above, or the pharmaceutical composition as described above.

In some embodiments, the disease or disorder is cancer.

In one aspect, the disclosure provides an article of manufacture comprising the engineered immune cell as described above, or the pharmaceutical composition as described above.

All embodiments presented herein are applicable to all aspects disclosed throughout the disclosure.

DETAILED DESCRIPTION

Figure 1A:
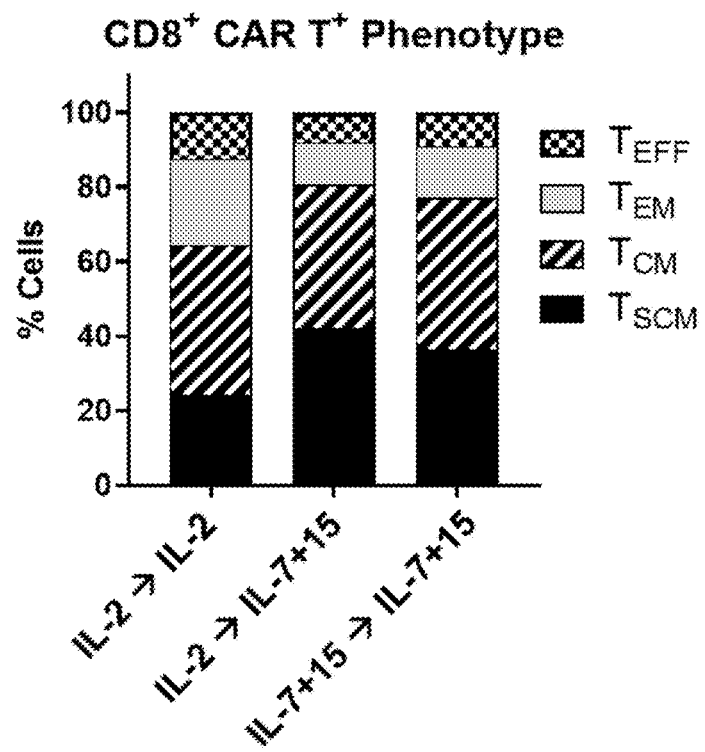
FIG. 1A depicts a comparison of CAR T⁺ phenotypes using processes comprising: sequential IL-2 stimulation; IL-2 stimulation followed by IL-7+IL-15 stimulation; and sequential IL-7+IL-15 stimulation. The IL-7+IL-15 based processes increase the abundance of $T_{SCM}$ CAR T cells.

Described herein are cell growth media and methods particularly useful for culturing immune cells.

Adoptive cell therapy using engineered immune cells is one type of immunotherapy that has emerged as a particularly promising new approach for cancer treatment. The production and manufacture of engineered immune cells comprises harvesting of immune cells (e.g., T cells) from a subject followed by in vitro cell expansion of the cells. Successful in vitro expansion of the immune cells (e.g., T cells) is characterized both by sufficient cell proliferation as well as the obtaining of desirable cell phenotypes.

For example, T cell expansion can result in a mixture of T cells that includes subsets of naïve T cells ($T_N$), memory T cells (including stem-cell like memory ($T_{SCM}$), central memory ($T_{CM}$), and effector memory ($T_{EM}$) T cells), and effector ($T_{EFF}$) T cells. The varying amounts of different T cell subsets can affect the therapeutic profile and efficacy of the resulting engineered T cells. In particular, T cell expansion methods that result in enriched amounts of T cells in early differentiation stages are therapeutically desirable.

Accordingly, cell growth media described herein can be particularly beneficial for T-cell expansion in which the proportion of $T_{SCM}$ and/or $T_{CM}$ is enriched. $T_{SCM}$ cells are the least-differentiated type of memory T cells and, for adoptive T-cell therapy, can be particularly advantageous in promoting prolonged in vivo T-cell proliferation following administration of the engineered cells to a patient. Accordingly, such cell culture media and immune cells (e.g., T cells) prepared using such media can result in more potent adoptive cell transfer therapies including CAR-T therapies as described herein.

In particular, cell growth media comprising combinations of different stimulants of cell proliferation (e.g., a first and a second T cell growth factor) in combination with an extracellular modulator of cell metabolism can result in desirable cell proliferation and cell phenotypes.

In one aspect, the disclosure features a cell growth medium (e.g., a medium suitable for T cell expansion) comprising:
- a first stimulant of cell proliferation (e.g., a first cytokine that stimulates T cell proliferation);
- a second stimulant of cell proliferation (e.g., a second cytokine that stimulates T cell proliferation); and
- an extracellular modulator of cell metabolism (e.g., T cell metabolism).

In particular, combinations and concentrations of cytokine and metabolic modulators as described herein provide new T cell expansion media can lead to increased potency of immune cell therapy products, including genetically-modified allogeneic cell therapy products and autologous cell therapy products. In one embodiment, the combination of IL-7 and IL-15 stimulants along with increased extracellular potassium can achieve improvements in obtaining desirable phenotypes of allogeneic CART cells (e.g., increased population of $T_{SCM}$ cells) and/or autologous cell therapy products as compared along with classical IL-2-based expansion conditions.

1. Immune Cells

Cells suitable for culturing using the media and methods described herein include immune cells.

Prior to the in vitro manipulation or genetic modification (e.g., as described herein), cells for use in methods described herein (e.g., immune cells) can be obtained from a subject. Cells can be obtained from a number of non-limiting sources, including peripheral blood mononuclear cells, bone marrow, lymph node tissue, cord blood, thymus tissue, stem cell- or iPSC-derived immune cells, tissue from a site of infection, ascites, pleural effusion, spleen tissue, and tumors. In some embodiments, any number of T cell lines available and known to those skilled in the art, can be used. In some embodiments, cells can be derived from a healthy donor, from a patient diagnosed with cancer or from a patient diagnosed with an infection. In some embodiments, cells can be part of a mixed population of cells which present different phenotypic characteristics.

In some embodiments, immune cells are obtained from a subject who will ultimately receive the engineered immune cells. In some embodiments, immune cells are obtained from a donor, who is a different individual from the subject who will receive the engineered immune cells.

In some embodiments, immune cells comprise T cells. T cells can be obtained from a number of sources, including peripheral blood mononuclear cells (PBMCs), bone marrow, lymph nodes tissue, cord blood, thymus tissue, stem cell- or iPSC-derived T cells, tissue from a site of infection, ascites, pleural effusion, spleen tissue, and tumors. In certain some embodiments, T cells can be obtained from a volume of blood collected from the subject using any number of techniques known to the skilled person, such as FICOLL™ separation.

Cells can be obtained from the circulating blood of an individual by apheresis. The apheresis product typically contains lymphocytes, including T cells, monocytes, granulocytes, B cells, other nucleated white blood cells, red blood cells, and platelets. In certain some embodiments, the cells collected by apheresis can be washed to remove the plasma fraction, and placed in an appropriate buffer or media for subsequent processing.

PBMCs can be used directly for genetic modification with the immune cells (such as CARs or TCRs) using methods as described herein. In certain some embodiments, after isolating the PBMCs, T lymphocytes can be further isolated and both cytotoxic and helper T lymphocytes can be sorted into naïve, memory, and effector T cell subpopulations either before or after genetic modification and/or expansion.

In certain some embodiments, T cells are isolated from PBMCs by lysing the red blood cells and depleting the monocytes, for example, using centrifugation through a PERCOLL™ gradient. A specific subpopulation of T cells, such as CCR7+, CD95+, CD122, CD27+, CD69+, CD127+, CD28+, CD3+, CD4+, CD8+, CD25+, CD62L+, CD45RA+, and CD45RO+ T cells can be further isolated by positive or negative selection techniques known in the art. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting can also be used to isolate cell populations of interest for use in the present disclosure.

In some embodiments, a population of T cells is enriched for C4+ cells.

In some embodiments, a population of T cells is enriched for CD8+ cells.

In some embodiments, CD8+ cells are further sorted into naive, central memory, and effector cells by identifying cell surface antigens that are associated with each of these types of CD8+ cells. In some embodiments, the expression of phenotypic markers of central memory T cells include CD45RO, CD62L, CCR7, CD28, CD3, and CD127 and are negative for granzyme B. In some embodiments, central memory T cells are CD45RO+, CD62L+, and/or CD8+ T cells. In some embodiments, effector T cells are negative for CD62L, CCR7, CD28, and/or CD127, and positive for granzyme B and perforin. In certain some embodiments, CD4+ T cells are further sorted into subpopulations. For example, CD4+T helper cells can be sorted into naive, central memory, and effector cells by identifying cell populations that have cell surface antigens.

It will be appreciated that PBMCs can further include other cytotoxic lymphocytes such as NK cells or NKT cells. An expression vector carrying the coding sequence of a chimeric receptor as disclosed herein can be introduced into a population of human donor T cells, NK cells or NKT cells. Successfully transduced T cells that carry the expression vector can be sorted using flow cytometry to isolate CD3 positive T cells and then further propagated to increase the number of these CAR expressing T cells in addition to cell activation using anti-CD3 antibodies and IL-2 or other methods known in the art as described elsewhere herein. Standard procedures are used for cryopreservation of T cells expressing the CAR for storage and/or preparation for use in a human subject. In one embodiment, the in vitro transduction, culture and/or expansion of T cells are performed in the absence of non-human animal derived products such as fetal calf serum and fetal bovine serum.

2. Engineered Immune Cells

Cell growth media and methods of use described herein can be particularly useful in in vitro expansion of immune cells, including engineered immune cells (e.g., CAR-T cells).

Engineered immune cells can be allogeneic or autologous.

In some embodiments, the engineered immune cell is a T cell (e.g. inflammatory T-lymphocyte cytotoxic T-lymphocyte, regulatory T-lymphocyte, helper T-lymphocyte, tumor infiltrating lymphocyte (TIL)), NK cell, NK-T-cell, TCR-expressing cell, dendritic cell, killer dendritic cell, a mast cell, or a B-cell. In some embodiments, the cell can be derived from the group consisting of CD4+T-lymphocytes and CD8+T-lymphocytes. In some exemplary embodiments, the engineered immune cell is a T cell.

In some embodiments, the engineered immune cell can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells.

In some embodiments, the cell is obtained or prepared from peripheral blood. In some embodiments, the cell is obtained or prepared from peripheral blood mononuclear cells (PBMCs). In some embodiments, the cell is obtained or prepared from bone marrow. In some embodiments, the cell is obtained or prepared from umbilical cord blood. In some embodiments, the cell is a human cell. In some embodiments, the cell is transfected or transduced by the nucleic acid vector using a method selected from the group consisting of electroporation, sonoporation, biolistics (e.g., Gene Gun), lipid transfection, polymer transfection, nanoparticles, or polyplexes.

a. Binding Agents (Including Antibodies)

In some embodiments, engineered immune cells comprise an antigen binding agent (e.g., comprising an antigen binding domain or comprising an antibody or fragment thereof).

As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CHI, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Those skilled in the art are well familiar with antibody structure and sequence elements, recognize "variable" and "constant" regions in provided sequences, and understand that there can be some flexibility in definition of a "boundary" between such domains such that different presentations of the same antibody chain sequence can, for example, indicate such a boundary at a location that is shifted one or a few residues relative to a different presentation of the same antibody chain sequence.

Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present disclosure include glycosylated Fc domains, including Fc domains with modified or engineered such glycosylation.

For purposes of the present disclosure, in certain some embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art.

Moreover, the term "antibody" as used herein, can refer in appropriate embodiments (unless otherwise stated or clear from context) to any of the art-known or developed constructs or formats for utilizing antibody structural and functional features in alternative presentation. For example, in some embodiments, an antibody utilized in accordance with the present disclosure is in a format selected from, but not limited to, intact IgA, IgG, IgE or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); camelid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-Bodies®; Affibodies®; TrimerX®; MicroProteins; Fynomers®, Centyrins®; and KALBITOR®s. In some embodiments, an antibody can lack a covalent modification (e.g., attachment of a glycan) that it would have if produced naturally. In some embodiments, an antibody can contain a covalent modification (e.g., attachment of a glycan, a payload (e.g., a detectable moiety, a therapeutic moiety, a catalytic moiety, etc.), or other pendant group (e.g., poly-ethylene glycol, etc.).

In some embodiments, the antibody or binding agent can be "symmetrical." By "symmetrical" is meant that the antibody or binding agent has the same kind of Fv regions (e.g., the antibody has two Fab regions). In some embodiments, the antibody or binding agent can be "asymmetrical." By "asymmetrical" is meant that the antibody or binding agent has at least two different kinds of Fv regions (e.g., the antibody has: Fab and scFv regions, Fab and scFv2 regions, or Fab-VHH regions). Various asymmetrical antibody or binding agent architectures are known in the art (Brinkman and Kontermann et al. 2017 Mabs (9)(2): 182-212).

As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent can include one or more constant region sequences that are characteristic of mouse, rabbit, primate, or human antibodies. In some embodiments, an antibody agent can include one or more sequence elements are humanized, primatized, chimeric, etc, as is known in the art. In many embodiments, the term "antibody agent" is used to refer to one or more of the art-known or developed constructs or formats for utilizing antibody structural and functional features in alternative presentation. For example, an antibody agent utilized in accordance with the present disclosure is in a format selected from, but not limited to, intact IgA, IgG, IgE or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-Bodies®; Affibodies®; TrimerX®; MicroProteins; Fynomers®, Centyrins®; and KALBITOR®s.

An antibody or antigen binding molecule encoded of the present disclosure can be single chained or double chained. In some embodiments, the antibody or antigen binding molecule is single chained. In certain some embodiments, the antigen binding molecule is selected from the group consisting of an scFv, a Fab, a Fab', a Fv, a F(ab')$_2$, a dAb, and any combination thereof.

Antibodies include antibody fragments. An antibody fragment comprises a portion of an intact antibody, such as the antigen binding or variable region of the intact antibody. Antibody fragments include, but are not limited to, Fab, Fab', Fab'-SH, F(ab')$_2$, Fv, diabody, linear antibodies, multispecific formed from antibody fragments antibodies and scFv fragments, and other fragments described below. Antibodies also include, but are not limited to, polyclonal monoclonal, chimeric dAb (domain antibody), single chain, $F_{ab}$, $F_a$, $F_{(ab)}$2 fragments, scFvs, and $F_{ab}$ expression libraries. An antibody can be a whole antibody, or immunoglobulin, or an antibody fragment. In some embodiments, the antibody is a full length antibody, e.g., an intact IgG1 antibody or other antibody class or isotype as described herein. (See, e.g., Hudson et al., Nat. Med., 9: 129-134 (2003); Pluckthun, The Pharmacology of Monoclonal Antibodies, vol. 113, pp. 269-315 (1994); Hollinger et al., Proc. Natl. Acad. Sci. USA, 90: 6444-6448 (1993); WO93/01161; and U.S. Pat. Nos. 5,571,894, 5,869,046, 6,248,516, and 5,587,458). A full length antibody, intact antibody, or whole antibody is an antibody having a structure substantially similar to a native antibody structure or having heavy chains that contain an Fc region as defined herein. Antibody fragments can be made by various techniques, including but not limited to proteolytic digestion of an intact antibody as well as production by recombinant host cells (e.g., E. coli or phage), as known in the art.

In some embodiments, an antibody is or comprises a monoclonal antibody, including a chimeric, humanized or human antibody.

In some embodiments, an antigen-specific antibody agent provided herein can be a chimeric antibody (See, e.g., U.S. Pat. No. 4,816,567; and Morrison et al., Proc. Natl. Acad. Sci. USA, 81:6851-6855 (1984)). A chimeric antibody can be an antibody in which a portion of the heavy and/or light chain is derived from a particular source or species, while the remainder of the heavy and/or light chain is derived from a different source or species. In one example, a chimeric antibody can comprise a non-human variable region (e.g., a variable region derived from a mouse, rat, hamster, rabbit, or non-human primate, such as a monkey) and a human constant region. In a further example, a chimeric antibody can be a "class switched" antibody in which the class or subclass has been changed from that of the parent antibody. Chimeric antibodies include antigen-binding fragments thereof.

In some embodiments, a chimeric antibody can be a humanized antibody (See, e.g., Almagro and Fransson, Front. Biosci., 13: 1619-1633 (2008); Riechmann et al., Nature, 332:323-329 (1988); Queen et al., Proc. Natl Acad. Sci. USA 86: 10029-10033 (1989); U.S. Pat. Nos. 5,821, 337, 7,527,791, 6,982,321, and 7,087,409; Kashmiri et al., Methods 36:25-34 (2005); Padlan, Mol. Immunol, 28:489-498 (1991); Dall'Acqua et al., Methods, 36:43-60 (2005); Osbourn et al., Methods, 36:61-68 (2005); and Klimka et al., Br. J. Cancer, 83:252-260 (2000)). A humanized antibody is a chimeric antibody comprising amino acid residues from non-human hypervariable regions and amino acid residues from human FRs. In certain some embodiments, a humanized antibody will comprise substantially all of at least one, and typically two, variable domains, in which all or substantially all of the hypervariable regions (e.g., CDRs) correspond to those of a non-human antibody, and all or substantially all of the FRs correspond to those of a human antibody. A humanized antibody optionally can comprise at least a portion of an antibody constant region derived from a human antibody.

A non-human antibody can be humanized to reduce immunogenicity to humans, while retaining the specificity and affinity of the parental non-human antibody. A humanized antibody can comprise one or more variable domains comprising one or more CDRs, or portions thereof, derived from a non-human antibody. A humanized antibody can comprise one or more variable domains comprising one or more FRs, or portions thereof, derived from human antibody sequences. A humanized antibody can optionally comprise at least a portion of a human constant region. In some embodiments, one or more FR residues in a humanized antibody are substituted with corresponding residues from a non-human antibody (e.g., the antibody from which the CDR residues are derived), to restore or improve antibody specificity or affinity.

Human framework regions that can be used for humanization include but are not limited to: framework regions selected using a "best-fit" method; framework regions derived from the consensus sequence of human antibodies of a particular subgroup of light or heavy chain variable regions; human mature (somatically mutated) framework regions or human germline framework regions; and framework regions derived from screening FR libraries (See, e.g., Sims et al., J. Immunol, 151:2296 (1993); Carter et al., Proc. Natl. Acad. Sci. USA, 89:4285 (1992); Presta et al., J. Immunol, 151:2623 (1993); Baca et al., J. Biol. Chem., 272: 10678-10684 (1997); and Rosok et al., J. Biol. Chem., 271:22611-22618 (1996)).

In some embodiments, an antibody agent provided herein is a human antibody. Human antibodies can be produced using various techniques known in the art (See, e.g., van Dijk and van de Winkel, Curr. Opin. Pharmacol, 5: 368-74 (2001); and Lonberg, Curr. Opin. Immunol, 20:450-459 (2008)). A human antibody can be one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be prepared by administering an immunogen to a transgenic animal that has been modified to produce intact human antibodies or intact antibodies with human variable regions in response to antigenic challenge (See, e.g., Lonberg, Nat. Biotech., 23: 1117-1125 (2005); U.S. Pat. Nos. 6,075,181, 6,150,584, 5,770,429, and 7,041, 870; and U.S. Pat. App. Pub. No. US 2007/0061900). Human variable regions from intact antibodies generated by such animals can be further modified, e.g., by combining with a different human constant region.

Human antibodies can also be made by hybridoma-based methods. For example, human antibodies can be produced from human myeloma and mouse-human heteromyeloma cell lines, using human B-cell hybridoma technology, and other methods (See, e.g., Kozbor, J. Immunol, 133: 3001 (1984); Brodeur et al., Monoclonal Antibody Production Techniques and Applications, pp. 51-63 (1987); Boerner et al., J. Immunol, 147: 86 (1991); Li et al., Proc. Natl. Acad. Sci. USA, 103:3557-3562 (2006); U.S. Pat. No. 7,189,826; Ni, Xiandai Mianyixue, 26(4): 265-268 (2006); Vollmers and Brandlein, Histology and Histopathology, 20(3): 927-937 (2005); and Vollmers and Brandlein, Methods and Findings in Experimental and Clinical Pharmacology, 27(3): 185-91 (2005)). Human antibodies can also be generated by isolating Fv clone variable domain sequences selected from human-derived phage display libraries. Such variable domain sequences can then be combined with a desired human constant region.

Modifications of the oligosaccharide in an antibody can be made, for example, to create antibody variants with certain improved properties. For example, antibody glycosylation variants can have improved CDC function. In some embodiments, the present disclosure can contemplate an antibody variant that possesses some but not all effector functions, which make it a desirable candidate for applications in which the half-life of the antibody in vivo is important yet certain effector functions (such as complement) are unnecessary or deleterious. In vitro and/or in vivo cytotoxicity assays can be conducted to confirm the reduction/depletion of CDC activities.

In some embodiments, an antibody agent provided herein can be further modified to contain additional nonproteinaceous moieties that are known in the art and readily available. The moieties suitable for derivatization of the antibody can include but are not limited to water soluble polymers. Non-limiting examples of water soluble polymers can include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethyl ene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde can have advantages in manufacturing due to its stability in water.

The polymer can be of any molecular weight, and can be branched or unbranched. The number of polymers attached to the antibody can vary, and if two or more polymers are attached, they can be the same or different molecules.

In some embodiments, conjugates of an antibody and nonproteinaceous moiety that can be selectively heated by exposure to radiation are provided. In some embodiments, the nonproteinaceous moiety can be a carbon nanotube (See, e.g., Kam et al., Proc. Natl. Acad. Sci. USA, 102: 11600-11605 (2005)). The radiation can be of any wavelength, and can include, but is not limited to, wavelengths that do not harm ordinary cells, but which heat the nonproteinaceous moiety to a temperature at which cells proximal to the antibody-nonproteinaceous moiety are killed.

b. Chimeric Antigen Receptors

In some embodiments, an engineered immune cell comprises a population of CARs, each CAR comprising an extracellular antigen-binding domain. In some embodiments, an immune cell comprises a population of CARs, each CAR comprising the same extracellular antigen-binding domains.

As used herein, chimeric antigen receptors (CARs) are proteins that specifically recognize target antigens (e.g., target antigens on cancer cells). When bound to the target antigen, the CAR can activate the immune cell to attack and destroy the cell bearing that antigen (e.g., the cancer cell). CARs can also incorporate costimulatory or signaling domains to increase their potency. See Krause et al., J. Exp. Med., Volume 188, No. 4, 1998 (619-626); Finney et al., *Journal of Immunology*, 1998, 161: 2791-2797, Song et al., Blood 119:696-706 (2012); Kalos et al., *Sci. Transl. Med.* 3:95 (2011); Porter et al., *N. Engl. J. Med.* 365:725-33 (2011), and Gross et al., *Annu. Rev. Pharmacol. Toxicol.* 56:59-83 (2016); U.S. Pat. Nos. 7,741,465, and 6,319,494.

Chimeric antigen receptors described herein comprise an extracellular domain, a transmembrane domain, and an intracellular domain, wherein the extracellular domain comprises an antigen binding domain that specifically binds to the target.

In some embodiments, antigen-specific CARs further comprise a safety switches and/or one or more monoclonal antibody specific-epitope.

i. Antigen Binding Domains

As discussed above, CARs described herein comprise an antigen binding domain. An "antigen binding domain" as used herein means any polypeptide that binds a specified target antigen. In some embodiments, the antigen binding domain binds to an antigen on a tumor cell. In some embodiments, the antigen binding domain binds to an antigen on a cell involved in a hyperproliferative disease.

In some embodiments, the antigen binding domain comprises a variable heavy chain, variable light chain, and/or one or more CDRs described herein. In some embodiments, the antigen binding domain is a single chain variable fragment (scFv), comprising light chain CDRs CDR1, CDR2 and CDR3, and heavy chain CDRs CDR1, CDR2 and CDR3.

Variants of the antigen binding domains (e.g., variants of the CDRs, VH and/or VL) are also within the scope of the disclosure, e.g., variable light and/or variable heavy chains that each have at least 70-80%, 80-85%, 85-90%, 90-95%, 95-97%, 97-99%, or above 99% identity to the amino acid sequences of antigen binding domain sequences. In some instances, such molecules include at least one heavy chain and one light chain, whereas in other instances the variant forms contain two variable light chains and two variable heavy chains (or subparts thereof). A skilled artisan will be able to determine suitable variants of the antigen binding domains as set forth herein using well-known techniques. In certain some embodiments, one skilled in the art can identify suitable areas of the molecule that can be changed without destroying activity by targeting regions not believed to be important for activity.

In certain some embodiments, the polypeptide structure of the antigen binding domains is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the antigen binding domain comprises or consists of avimers.

An antigen binding domain is said to be "selective" when it binds to one target more tightly than it binds to a second target.

In some embodiments, an antigen binding domain is a scFv.

In some embodiments, an antigen-selective CAR comprises a leader or signal peptide In other embodiments, the disclosure relates to isolated polynucleotides encoding any one of the antigen binding domains described herein. In some embodiments, the disclosure relates to isolated polynucleotides encoding a CAR. Also provided herein are vectors comprising the polynucleotides, and methods of making same.

ii. Safety Switches and Monoclonal Antibody Specific-Epitopes

It will be appreciated that adverse events can be minimized by transducing the immune cells (containing one or more CARs) with a suicide gene. It can also be desired to incorporate an inducible "on" or "accelerator" switch into the immune cells. Suitable techniques include use of inducible caspase-9 (U.S. Appl. 2011/0286980) or a thymidine kinase, before, after or at the same time, as the cells are transduced with the CAR construct of the present disclosure. Additional methods for introducing suicide genes and/or "on" switches include TALENS, zinc fingers, RNAi, siRNA, shRNA, antisense technology, and other techniques known in the art.

In accordance with the disclosure, additional on-off or other types of control switch techniques can be incorporated herein. These techniques can employ the use of dimerization domains and optional activators of such domain dimerization. These techniques include, e.g., those described by Wu et al., Science 2014 350 (6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of which are also incorporated by reference herein in their entirety. Additional dimerization pairs can include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology can be found in e.g., WO 2014/127261, WO 2015/090229, US 2014/0286987, US2015/0266973, US2016/0046700, U.S. Pat. No. 8,486,693, US 2014/0171649, and US 2012/0130076, the contents of which are further incorporated by reference herein in their entirety.

In some embodiments, the CAR-immune cell (e.g., CAR-T cell) of the disclosure comprises a polynucleotide encoding a suicide polypeptide, such as for example RQR8. See, e.g., WO2013153391A, which is hereby incorporated by reference in its entirety. In CAR-immune cell (e.g., CAR-T cell) cells comprising the polynucleotide, the suicide polypeptide is expressed at the surface of a CAR-immune cell (e.g., CAR-T cell). In some embodiments, the suicide polypeptide comprises the amino acid sequence shown in SEQ ID NO: 1.

(SEQ ID NO: 1)
CPYSNPSLCSGGGGSELPTQGTFSNVSTNVSPAKPTTTACPYSNPSLCSG

GGGSPAPRPPTPAPTIASQPLSLRPEACRPAAGGAVHTRGLDFACDIYIW

APLAGTCGVLLLSLVITLYCNHRNRRRVCKCPRPVV.

The suicide polypeptide can also comprise a signal peptide at the amino terminus—for example, MGTSLLCWMALCLLGADHADA (SEQ ID NO: 2). In some embodiments, the suicide polypeptide comprises the amino acid sequence shown in SEQ ID NO: 3, which includes the signal sequence of SEQ ID NO: 2.

(SEQ ID NO: 3)
MGTSLLCWMALCLLGADHADACPYSNPSLCSGGGGSELPTQGTFSNVSTN

VSPAKPTTTACPYSNPSLCSGGGGSPAPRPPTPAPTIASQPLSLRPEACR

PAAGGAVHTRGLDFACDIYIWAPLAGTCGVLLLSLVITLYCNHRNRRRVC

KCPRPVV.

When the suicide polypeptide is expressed at the surface of a CAR-immune cell (e.g., CAR-T cell), binding of rituximab to the R epitopes of the polypeptide causes lysis of the cell. More than one molecule of rituximab can bind per polypeptide expressed at the cell surface. Each R epitope of the polypeptide can bind a separate molecule of rituximab. Deletion of antigen-specific CAR-immune cell (e.g., CAR-T cell) can occur in vivo, for example by administering rituximab to a patient. The decision to delete the transferred cells can arise from undesirable effects being detected in the patient which are attributable to the transferred cells, such as for example, when unacceptable levels of toxicity are detected.

In some embodiments, a suicide polypeptide is expressed on the surface of the cell. In some embodiments, a suicide polypeptide is included in the CAR construct. In some embodiments, a suicide polypeptide is not part of the CAR construct.

In some embodiments, the extracellular domain of an antigen-specific CARs can comprise one or more epitopes specific for (i.e., specifically recognized by) a monoclonal antibody. These epitopes are also referred to herein as mAb-specific epitopes. Exemplary mAb-specific epitopes are disclosed in International Patent Publication No. WO 2016/120216, which is incorporated herein in its entirety. In these embodiments, the extracellular domain of the CARs comprise antigen binding domains that specifically bind to an antigen and one or more epitopes that bind to one or more monoclonal antibodies (mAbs). CARs comprising the mAb-specific epitopes can be single-chain or multi-chain.

The inclusion of epitopes specific for monoclonal antibodies in the extracellular domain of the CARs described herein allows sorting and depletion of engineered immune cells expressing the CARs. In some embodiments, this feature also promotes recovery of endogenous antigen-expressing cells that were depleted by administration of engineered immune cells expressing the CARs. In some embodiments, allowing for depletion provides a safety switch in case of deleterious effects, e.g., upon administration to a subject.

Accordingly, in some embodiments, the present disclosure relates to a method for sorting and/or depleting the engineered immune cells endowed with the CARs comprising mAb-specific epitopes and a method for promoting recovery of endogenous antigen-expressing cells.

Several epitope-monoclonal antibody couples can be used to generate CARs comprising monoclonal antibody specific epitopes; in particular, those already approved for medical use, such as CD20 epitope/rituximab as a non-limiting example.

The antigen also encompasses methods for sorting the engineered immune cells endowed with the antigen-specific CARs expressing the mAb-specific epitope(s) and therapeutic methods where the activation of the engineered immune cells endowed with these CARs is modulated by depleting the cells using an antibody that targets the external ligand binding domain of said CARs. Table 1 provides exemplary mimotope sequences that can be inserted into the extracellular domains of any one of the CARs of the disclosure.

TABLE 1

Exemplary mimotope sequences

Rituximab

| Mimotope | SEQ ID NO: 4 | CPYSNPSLC |

Palivizumab

| Epitope | SEQ ID NO: 5 | NSELLSLINDMPITNDQKKLMSNN |

Cetuximab

| Mimotope 1 | SEQ ID NO: 6 | CQFDLSTRRLKC |
| Mimotope 2 | SEQ ID NO: 7 | CQYNLSSRALKC |
| Mimotope 3 | SEQ ID NO: 8 | CVWQRWQKSYVC |
| Mimotope 4 | SEQ ID NO: 9 | CMWDRFSRWYKC |

Nivolumab

| Epitope 1 | SEQ ID NO: 10 | SFVLNWYRMSPSNQTDKLAAFPEDR |
| Epitope 2 | SEQ ID NO: 11 | SGTYLCGAISLAPKAQIKE |

TABLE 1-continued

Exemplary mimotope sequences

QBEND-10

| Epitope 1 | SEQ ID NO: 12 | ELPTQGTFSNVSTNVS |
| Epitope 2 | SEQ ID NO: 25 | ELPTQGTFSNVSTNVSPAKPTTTA |

Alemtuzumab

| Epitope | SEQ ID NO: 13 | GQNDTSQTSSPS |

In some embodiments, the extracellular binding domain of the CAR comprises the following sequence $V_1$-$L_1$-$V_2$-$(L)_x$-Epitope1-$(L)_x$-;
$V_1$-$L_1$-$V_2$-$(L)_x$-Epitope1-$(L)_x$-Epitope2-$(L)_x$-;
$V_1$-$L_1$-$V_2$-$(L)_x$-Epitope1-$(L)_x$-Epitope2-$(L)_x$-Epitope3-$(L)_x$-;
$(L)_x$-Epitope1-$(L)_x$-$V_1$-$L_1$-$V_2$;
$(L)_x$-Epitope1-$(L)_x$-Epitope2-$(L)_x$-$V_1$-$L_1$-$V_2$;
Epitope1-$(L)_x$-Epitope2-$(L)_x$-Epitope3-$(L)_x$-$V_1$-$L_1$-$V_2$;
$(L)_x$-Epitope1-$(L)_x$-$V_1$-$L_1$-$V_2$-$(L)_x$-Epitope2-$(L)_x$;
$(L)_x$-Epitope1-$(L)_x$-$V_1$-$L_1$-$V_2$-$(L)_x$-Epitope2-$(L)_x$-Epitope3-$(L)_x$-;
$(L)_x$-Epitope1-$(L)_x$-$V_1$-$L_1$-$V_2$-$(L)_x$-Epitope2-$(L)_x$-Epitope3-$(L)_x$-Epitope4-$(L)_x$;
$(L)_x$-Epitope1-$(L)_x$-Epitope2-$(L)_x$-$V_1$-$L_1$-$V_2$-$(L)_x$-Epitope3-$(L)_x$;
$(L)_x$-Epitope1-$(L)_x$-Epitope2-$(L)_x$-$V_1$-$L_1$-$V_2$-$(L)_x$-Epitope3-$(L)_x$-Epitope4-$(L)_x$;
$V_1$-$(L)_x$-Epitope1-$(L)_x$-$V_2$;
$V_1$-$(L)_x$-Epitope1-$(L)_x$-$V_2$-$(L)_x$-Epitope2-$(L)_x$;
$V_1$-$(L)_x$-Epitope1-$(L)_x$-$V_2$-$(L)_x$-Epitope2-$(L)_x$-Epitope3-$(L)_x$;
$V_1$-$(L)_x$-Epitope1-$(L)_x$-$V_2$-$(L)_x$-Epitope2-$(L)_x$-Epitope3-$(L)_x$-Epitope4-$(L)_x$;
$(L)_x$-Epitope1-$(L)_x$-$V_1$-$(L)_x$-Epitope2-$(L)_x$-$V_2$; or,
$(L)_x$-Epitope1-$(L)_x$-$V_1$-$(L)_x$-Epitope2-$(L)_x$-$V_2$-$(L)_x$-Epitope3-$(L)_x$;

wherein,
$V_1$ is $V_L$ and $V_2$ is $V_H$ or $V_1$ is $V_H$ and $V_2$ is $V_L$;
$L_1$ is a linker suitable to link the $V_H$ chain to the $V_L$ chain;
Epitope 1, Epitope 2, Epitope 3 and Epitope 4 are mAb-specific epitopes and can be identical or different and wherein $V_H$ is an heavy chain variable fragment and $V_L$ is a light chain variable fragment.

iii. Hinge Domain

The extracellular domain of the CARs of the disclosure can comprise a "hinge" domain (or hinge region). The term generally to any polypeptide that functions to link the transmembrane domain in a CAR to the extracellular antigen binding domain in a CAR. In particular, hinge domains can be used to provide more flexibility and accessibility for the extracellular antigen binding domain.

A hinge domain can comprise up to 300 amino acids—in some embodiments 10 to 100 amino acids or in some embodiments 25 to 50 amino acids. The hinge domain can be derived from all or part of naturally occurring molecules, such as from all or part of the extracellular region of CD8, CD4, CD28, 4-1BB, or IgG (in particular, the hinge region of an IgG; it will be appreciated that the hinge region can contain some or all of a member of the immunoglobulin family such as IgG1, IgG2, IgG3, IgG4, IgA, IgD, IgE, IgM, or fragment thereof), or from all or part of an antibody heavy-chain constant region. Alternatively the A domain can be a synthetic sequence that corresponds to a naturally occurring A sequence, or can be an entirely synthetic A sequence. In some embodiments said A domain is a part of human CD8α chain (e.g., NP_001139345.1). In another particular embodiment, said hinge and transmembrane domains comprise a part of human CD8α chain. In some embodiments, the hinge domain of CARs described herein comprises a subsequence of CD8α, an IgG1, IgG4, PD-1 or an FcγRIIIα, in particular the hinge region of any of an CD8α, an IgG1, IgG4, PD-1 or an FcγRIIIα. In some embodiments, the hinge domain comprises a human CD8a hinge, a human IgG1 hinge, a human IgG4, a human PD-1 or a human FcγRIIIα hinge. In some embodiments the CARs disclosed herein comprise a scFv, CD8α human hinge and transmembrane domains, the CD3ζ signaling domain, and 4-1BB signaling domain. Table 2 provides amino acid sequences for exemplary hinges provided herein.

TABLE 2

Exemplary Hinges

| Domain | Amino Acid Sequence | SEQ ID NO: |
|---|---|---|
| FcγRIIIα hinge | GLAVSTISSFFPPGYQ | 14 |
| CD8α hinge | TTTPAPRPPTPAPTIASQPLSLRPEACRPA AGGAVHTRGLDFACD | 15 |
| IgG1 hinge | EPKSPDKTHTCPPCPAPPVAGPSVFLFPPK PKDTLMIARTPEVTCVVDVSHEDPEVKFNW YVDGVEVHNAKTKPREEQYNSTYRVVSVLT VLHQDWLNGKEYKCKVSNKALPAPIEKTIS KAKGQPREPQVYTLPPSRDELTKNQVSLTC LVKGFYPSDIAVEWESNGQPENNYKTTPPV LDSDGSFFLYSKLTVDKSRWQQGNVFSCSV MHEALHNHYTQKSLSLSPGK | 16 | iv. Transmembrane Domain

The CARs of the disclosure are designed with a transmembrane domain that is fused to the extracellular domain of the CAR. It can similarly be fused to the intracellular domain of the CAR. In some instances, the transmembrane domain can be selected or modified by amino acid substitution to avoid binding of such domains to the transmembrane domains of the same or different surface membrane proteins to minimize interactions with other members of the receptor complex. In some embodiments, short linkers can form linkages between any or some of the extracellular, transmembrane, and intracellular domains of the CAR.

Suitable transmembrane domains for a CAR disclosed herein have the ability to (a) be expressed at the surface an immune cell such as, for example without limitation, a lymphocyte cell, such as a T helper ($T_h$) cell, cytotoxic T ($T_c$) cell, T regulatory ($T_{reg}$) cell, or Natural killer (NK) cells, and/or (b) interact with the extracellular antigen binding domain and intracellular signaling domain for directing the cellular response of an immune cell against a target cell.

The transmembrane domain can be derived either from a natural or from a synthetic source. Where the source is natural, the domain can be derived from any membrane-bound or transmembrane protein.

Transmembrane regions of particular use in this disclosure can be derived from (comprise, or correspond to) CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 1d, ITGAE, CD103, ITGAL, CD11a, LFA-1, ITGAM, CD1 1b, ITGAX, CD1 1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

As non-limiting examples, the transmembrane region can be a derived from, or be a portion of a T cell receptor such as α, β, γ or δ, polypeptide constituting CD3 complex, IL-2 receptor p55 (α chain), p75 (β chain) or γ chain, subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8α chain (e.g., NP_001139345.1).

In some embodiments, the transmembrane domain in the CAR of the disclosure is a CD8α transmembrane domain. In some embodiments, the transmembrane domain in the CAR of the disclosure is a CD8α transmembrane domain comprising the amino acid sequence IYIWAPLAGTCGVLLLSLVIT (SEQ ID NO: 17). In some embodiments, the CD8α transmembrane domain comprises the nucleic acid sequence that encodes the transmembrane amino acid sequence of SEQ ID NO: 17. In some embodiments, the hinge and transmembrane domain in the CAR of the disclosure is a CD8α hinge and transmembrane domain comprising the amino acid sequence of SEQ ID NO: 17.

In some embodiments, the transmembrane domain in the CAR of the disclosure is a CD28 transmembrane domain. In some embodiments, the transmembrane domain in the CAR of the disclosure is a CD28 transmembrane domain comprising the amino acid sequence of FWVLVVVGGVLACYSLLVTVAFIIFWV (SEQ ID NO: 18). In some embodiments, the CD28 transmembrane domain comprises the nucleic acid sequence that encodes the transmembrane amino acid sequence of SEQ ID NO: 18.

v. Intracellular Domain

The intracellular (cytoplasmic) domain of the CARs of the disclosure can provide activation of at least one of the normal effector functions of the immune cell comprising the CAR. Effector function of a T cell, for example, can refer to cytolytic activity or helper activity, including the secretion of cytokines.

In some embodiments, an activating intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability.

It will be appreciated that suitable (e.g., activating) intracellular domains include, but are not limited to signaling domains derived from (or corresponding to) CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 1d, ITGAE, CD103, ITGAL, CD1 1a, LFA-1, ITGAM, CD1 1b, ITGAX, CD1 1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

The intracellular domains of the CARs of the disclosure can incorporate, in addition to the activating domains described above, co-stimulatory signaling domains (interchangeably referred to herein as costimulatory molecules) to increase their potency. Costimulatory domains can provide a signal in addition to the primary signal provided by an activating molecule as described herein.

It will be appreciated that suitable costimulatory domains within the scope of the disclosure can be derived from (or correspond to) for example, CD28, OX40, 4-1BB/CD137, CD2, CD3 (alpha, beta, delta, epsilon, gamma, zeta), CD4, CD5, CD7, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CD1 1a/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNFR, integrin, signaling lymphocytic activation molecule, BTLA, Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1-1d, ITGAE, CD103, ITGAL, CD1-1a, LFA-1, ITGAM, CD1-1b, ITGAX, CD1-1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof. It will be appreciated that additional costimulatory molecules, or fragments thereof, not listed above are within the scope of the disclosure.

In some embodiments, the intracellular/cytoplasmic domain of the CAR can be designed to comprise the 4-1BB/CD137 domain by itself or combined with any other desired intracellular domain(s) useful in the context of the CAR of the disclosure. The complete native amino acid sequence of 4-1BB/CD137 is described in NCBI Reference Sequence: NP_001552.2. The complete native 4-1BB/CD137 nucleic acid sequence is described in NCBI Reference Sequence: NM_001561.5.

In some embodiments, the intracellular/cytoplasmic domain of the CAR can be designed to comprise the CD28 domain by itself or combined with any other desired intracellular domain(s) useful in the context of the CAR of the disclosure. The complete native amino acid sequence of CD28 is described in NCBI Reference Sequence: NP_006130.1. The complete native CD28 nucleic acid sequence is described in NCBI Reference Sequence: NM_006139.1.

In some embodiments, the intracellular/cytoplasmic domain of the CAR can be designed to comprise the CD3 zeta domain by itself or combined with any other desired intracellular domain(s) useful in the context of the CAR of the disclosure. In some embodiments, the intracellular signaling domain of the CAR can comprise the CD3ζ signaling domain which has amino acid sequence with at least about 70%, at least 80%, at least 90%, 95%, 97%, or 99% sequence identity with an amino acid sequence shown in SEQ ID NO: 19 or SEQ ID NO: 26.

(SEQ ID NO: 19)
LRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKD

TYDALHMQALPPR (SEQ ID NO: 26)
LRVKFSRSADAPAYKQGQNQLYNELNLGRREEYDVLDKRRGRDPEMGGKP

RRKNPQEGLYNELQKDKMAEAYSEIGMKGERRRGKGHDGLYQGLSTATKD

TYDALHMQALPPR

For example, the intracellular domain of the CAR can comprise a CD3 zeta chain portion and a portion of a costimulatory signaling molecule. The intracellular signaling sequences within the intracellular signaling portion of the CAR of the disclosure can be linked to each other in a random or specified order. In some embodiments, the intracellular domain is designed to comprise the activating domain of CD3 zeta and a signaling domain of CD28. In some embodiments, the intracellular domain is designed to comprise the activating domain of CD3 zeta and a signaling domain of 4-1BB.

In some embodiments, the 4-1BB (intracellular domain) comprises the amino acid sequence (SEQ ID NO: 20)
KRGRKKLLYIFKQPFMRPVQTTQEEDGCSCRFPEEEEGGCEL.

In some embodiments, the 4-1BB (intracellular domain) is encoded by the nucleic acid sequence:

(SEQ ID NO: 21)
AAGCGCGGCAGGAAGAAGCTCCTCTACATTTTTAAGCAGCCTTTTATGAG

GCCCGTACAGACAACACAGGAGGAAGATGGCTGTAGCTGCAGATTTCCCG

AGGAGGAGGAAGGTGGGTGCGAGCTG.

In some embodiments, the intracellular domain in the CAR is designed to comprise a portion of CD28 and CD3 zeta, wherein the intracellular CD28 comprises the nucleic acid sequence set forth in SEQ ID NO: 22.

```
                                                 (SEQ ID NO: 22)
AGATCCAAAAGAAGCCGCCTGCTCCATAGCGATTACATGAATATGACTCC

ACGCCGCCCTGGCCCCACAAGGAAACACTACCAGCCTTACGCACCACCTA

GAGATTTCGCTGCCTATCGGAGC.
```

In some embodiments, the intracellular domain in the CAR is designed to comprise the amino acid sequence RSKRSRLLHSDYMNMTPRRPGPTRKHYQPYAPPRD-FAAYRS (SEQ ID NO: 23). The CD3 zeta amino acid sequence can comprise SEQ ID NO: 23 and the nucleic acid sequence can comprise SEQ ID NO: 24:

```
                                                 (SEQ ID NO: 24)
AGGGTGAAGTTTTCCAGATCTGCAGATGCACCAGCGTATCAGCAGGGCCA

GAACCAACTGTATAACGAGCTCAACCTGGGACGCAGGGAAGAGTATGACG

TTTTGGACAAGCGCAGAGGACGGGACCCTGAGATGGGTGGCAAACCAAGA

CGAAAAAACCCCCAGGAGGGTCTCTATAATGAGCTGCAGAAGGATAAGAT

GGCTGAAGCCTATTCTGAAATAGGCATGAAAGGAGAGCGGAGAAGGGGAA

AAGGGCACGACGGTTTGTACCAGGGACTCAGCACTGCTACGAAGGATACT

TATGACGCTCTCCACATGCAAGCCCTGCCACCTAGG.
```

In some embodiments the intracellular signaling domain of the CAR of the disclosure comprises a domain of a co-stimulatory molecule. In some embodiments, the intracellular signaling domain of a CAR of the disclosure comprises a part of co-stimulatory molecule selected from the group consisting of fragment of 4-1BB (GenBank: AAA53133.) and CD28 (NP_006130.1). In some embodiments, the intracellular signaling domain of the CAR of the disclosure comprises amino acid sequence which comprises at least 70%, at least 80%, at least 90%, 95%, 97%, or 99% sequence identity with an amino acid sequence shown in SEQ ID NO: 20 and SEQ ID NO: 22. In some embodiments, the intracellular signaling domain of the CAR of the disclosure comprises an amino acid sequence which comprises at least 70%, at least 80%, at least 90%, 95%, 97%, or 99% sequence identity with an amino acid sequence shown in SEQ ID NO: 20 and/or at least 70%, at least 80%, at least 90%, 95%, 97%, or 99% sequence identity with an amino acid sequence shown in SEQ ID NO: 22.

c. Immune Cells Comprising CARs

Provided herein are engineered immune cells expressing the CARs of the disclosure (e.g., CAR-T cells).

In some embodiments, an engineered immune cell comprises a population of CARs, each CAR comprising extracellular antigen-binding domains. In some embodiments, an engineered immune cell comprises a population of CARs, each CAR comprising different extracellular antigen-binding domains. In some embodiments, an immune cell comprises a population of CARs, each CAR comprising the same extracellular antigen-binding domains.

The engineered immune cells can be allogeneic or autologous.

In some embodiments, the engineered immune cell is a T cell (e.g., inflammatory T-lymphocyte cytotoxic T-lymphocyte, regulatory T-lymphocyte, helper T-lymphocyte, tumor infiltrating lymphocyte (TIL)), NK cell, NK-T-cell, TCR-expressing cell, dendritic cell, killer dendritic cell, a mast cell, or a B-cell. In some embodiments, the cell can be derived from the group consisting of CD4+ T-lymphocytes and CD8+ T-lymphocytes. In some exemplary embodiments, the engineered immune cell is a T cell. In some exemplary embodiments, the engineered immune cell is a gamma delta T cell. In some exemplary embodiments, the engineered immune cell is a macrophage.

In some embodiments, the engineered immune cell can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells.

In some embodiments, the cell is obtained or prepared from peripheral blood. In some embodiments, the cell is obtained or prepared from peripheral blood mononuclear cells (PBMCs). In some embodiments, the cell is obtained or prepared from bone marrow. In some embodiments, the cell is obtained or prepared from umbilical cord blood. In some embodiments, the cell is a human cell. In some embodiments, the cell is transfected or transduced by the nucleic acid vector using a method selected from the group consisting of electroporation, sonoporation, biolistics (e.g., Gene Gun), lipid transfection, polymer transfection, nanoparticles, viral transfection (e.g., retrovirus, lentivirus, AAV) or polyplexes.

In some embodiments, the engineered immune cells expressing at their cell surface membrane an antigen-specific CAR of the disclosure comprise a percentage of stem cell memory and central memory cells greater than 10%, 20%, 30%, 40%, 50%, 60%, 70%, 80%, 90%, or 100%.

In some embodiments, the engineered immune cells expressing at their cell surface membrane an antigen-specific CAR of the disclosure comprise a percentage of stem cell memory and central memory cells of about 10% to about 100%, about 10% to about 90%, about 10% to about 80%, about 10% to about 70%, about 10% to about 60%, about 10% to about 50%, about 10% to about 40%, about 10% to about 30%, about 10% to about 20%, about 15% to about 100%, about 15% to about 90%, about 15% to about 80%, about 15% to about 70%, about 15% to about 60%, about 15% to about 50%, about 15% to about 40%, about 15% to about 30%, about 20% to about 100%, about 20% to about 90%, about 20% to about 80%, about 20% to about 70%, about 20% to about 60%, about 20% to about 50%, about 20% to about 40%, about 20% to about 30%, about 30% to about 100%, about 30% to about 90%, about 30% to about 80%, about 30% to about 70%, about 30% to about 60%, about 30% to about 50%, about 30% to about 40%, about 40% to about 100%, about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 90%, about 70% to about 80%, about 80% to about 100%, about 80% to about 90%, about 90% to about 100%, about 25% to about 50%, about 75% to about 100%, or about 50% to about 75%.

In some embodiments, the engineered immune cells expressing at their cell surface membrane an antigen-specific CAR of the disclosure comprise a percentage of stem cell memory and central memory cells greater than 10%, 20%, 30%, 40%, 50%, or 60%.

In some embodiments, the engineered immune cells expressing at their cell surface membrane an antigen-specific CAR of the disclosure comprise a percentage of stem cell memory and central memory cells of about 10% to about 60%, about 10% to about 50%, about 10% to about 40%, about 15% to about 50%, about 15% to about 40%, about 20% to about 60%, or about 20% to about 70%.

In some embodiments, the engineered immune cells expressing at their cell surface membrane an antigen-specific CAR of the disclosure are enriched in $T_{CM}$ and/or $T_{SCM}$ cells such that the engineered immune cells comprise at least about 60%, 65%, 70%, 75%, or 80% combined $T_{CM}$ and $T_{SCM}$ cells. In some embodiments, the engineered immune cells expressing at their cell surface membrane an antigen-specific CAR of the disclosure are enriched in $T_{CM}$ and/or $T_{SCM}$ cells such that the engineered immune cells comprise at least about 70% combined $T_{CM}$ and $T_{SCM}$ cells. In some embodiments, the engineered immune cells expressing at their cell surface membrane an antigen-specific CAR of the disclosure are enriched in $T_{CM}$ and/or $T_{SCM}$ cells such that the engineered immune cells comprise at least about 75% combined $T_{CM}$ and/or $T_{SCM}$ cells.

In some embodiments, the engineered immune cells expressing at their cell surface membrane an antigen-specific CAR of the disclosure are enriched in $T_{CM}$ and/or $T_{SCM}$ cells such that the engineered immune cells comprise at least about 20%, 25%, 30%, 35%, 40%, 45%, 50%, 55%, or 60% $T_{SCM}$ cells. In some embodiments, the engineered immune cells expressing at their cell surface membrane an antigen-specific CAR of the disclosure are enriched in $T_{CM}$ and/or $T_{SCM}$ cells such that the engineered immune cells comprise at least about 30%, 35%, 40%, or 45% $T_{SCM}$ cells.

In some embodiments, the immune cell is an inflammatory T-lymphocyte that expresses any one of the CARs described herein. In some embodiments, the immune cell is a cytotoxic T-lymphocyte that expresses any one of the CARs described herein. In some embodiments, the immune cell is a regulatory T-lymphocyte that expresses any one of the CARs described herein. In some embodiments, the immune cell is a helper T-lymphocyte that expresses any one of the CARs described herein.

Also provided herein are cell lines obtained from a transformed immune cell (e.g., T-cell) according to any of the above-described methods. Also provided herein are modified cells resistant to an immunosuppressive treatment. In some embodiments, an isolated cell according to the disclosure comprises a polynucleotide encoding a CAR.

In some embodiments, an engineered immune cell according to the present disclosure can comprise one or more disrupted or inactivated genes. In some embodiments, an engineered immune cell according to the present disclosure comprises one disrupted or inactivated gene selected from the group consisting of CD52, DLL3, GR, PD-1, CTLA-4, LAG3, TIM3, BTLA, BY55, TIGIT, B7H5, LAIR1, SIGLEC10, 2B4, HLA, TCRα and TCRβ and/or expresses a CAR, a multi-chain CAR and/or a pTα transgene. In some embodiments, an isolated cell comprises polynucleotides encoding polypeptides comprising a multi-chain CAR. In some embodiments, the isolated cell according to the present disclosure comprises two disrupted or inactivated genes selected from the group consisting of: CD52 and GR, CD52 and TCRα, CDR52 and TCRβ, DLL3 and CD52, DLL3 and TCRα, DLL3 and TCRβ, GR and TCRα, GR and TCRβ, TCRα and TCRβ, PD-1 and TCRα, PD-1 and TCRβ, CTLA-4 and TCRα, CTLA-4 and TCRβ, LAG3 and TCRα, LAG3 and TCRβ, TIM3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ and/or expresses a CAR, a multi-chain CAR and a pTα transgene. In some embodiments the method comprises disrupting or inactivating one or more genes by introducing into the cells an endonuclease able to selectively inactivate a gene by selective DNA cleavage. In some embodiments the endonuclease can be, for example, a zinc finger nuclease (ZFN), megaTAL nuclease, meganuclease, transcription activator-like effector nuclease (TALE-nuclease), or CRIPR (e.g., Cas9) endonuclease.

In some embodiments, TCR is rendered not functional in the cells according to the disclosure by disrupting or inactivating TCRα gene and/or TCRβ gene(s). In some embodiments, a method to obtain modified cells derived from an individual is provided, wherein the cells can proliferate independently of the major histocompatibility complex (MHC) signaling pathway. Modified cells, which can proliferate independently of the MHC signaling pathway, susceptible to be obtained by this method are encompassed in the scope of the present disclosure. Modified cells disclosed herein can be used in for treating patients in need thereof against Host versus Graft (HvG) rejection and Graft versus Host Disease (GvHD); therefore in the scope of the present disclosure is a method of treating patients in need thereof against Host versus Graft (HvG) rejection and Graft versus Host Disease (GvHD) comprising treating said patient by administering to said patient an effective amount of modified cells comprising disrupted or inactivated TCRα and/or TCRβ genes.

In some embodiments, the immune cells are engineered to be resistant to one or more chemotherapy drugs. The chemotherapy drug can be, for example, a purine nucleotide analogue (PNA), thus making the immune cell suitable for cancer treatment combining adoptive immunotherapy and chemotherapy. Exemplary PNAs include, for example, clofarabine, fludarabine, cyclophosphamide, and cytarabine, alone or in combination. PNAs are metabolized by deoxycytidine kinase (dCK) into mono-, di-, and tri-phosphate PNA. Their tri-phosphate forms compete with ATP for DNA synthesis, act as pro-apoptotic agents, and are potent inhibitors of ribonucleotide reductase (RNR), which is involved in trinucleotide production.

In some embodiments, isolated cells or cell lines of the disclosure can comprise a pTα or a functional variant thereof. In some embodiments, an isolated cell or cell line can be further genetically modified by disrupting or inactivating the TCRα gene.

The disclosure also provides engineered immune cells comprising any of the CAR polynucleotides described herein. In some embodiments, a CAR can be introduced into an immune cell as a transgene via a plasmid vector. In some embodiments, the plasmid vector can also contain, for example, a selection marker which provides for identification and/or selection of cells which received the vector.

CAR polypeptides can be synthesized in situ in the cell after introduction of polynucleotides encoding the CAR polypeptides into the cell. Alternatively, CAR polypeptides can be produced outside of cells, and then introduced into cells. Methods for introducing a polynucleotide construct into cells are known in the art. In some embodiments, stable transformation methods (e.g., using a lentiviral vector) can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides can be introduced into a cell by any suitable means such as for example, recombinant viral vectors (e.g., retroviruses, adenoviruses), liposomes, and the like. Transient transformation methods include, for example without limitation, microinjection, electroporation or particle bombardment. Polynucleotides can be included in vectors, such as for example plasmid vectors or viral vectors.

In some embodiments, isolated nucleic acids are provided comprising a promoter operably linked to a first polynucleotide encoding an antigen binding domain, at least one costimulatory molecule, and an activating domain. In some embodiments, the nucleic acid construct is contained within a viral vector. In some embodiments, the viral vector is selected from the group consisting of retroviral vectors, murine leukemia virus vectors, SFG vectors, adenoviral vectors, lentiviral vectors, adeno-associated virus (AAV) vectors, Herpes virus vectors, and vaccinia virus vectors. In some embodiments, the nucleic acid is contained within a plasmid.

3. Cell Growth Media for In Vitro Expansion of Immune Cells

In vitro expansion of cells (including expansion of immune cells such as genetically modified T cells) can be achieved using a cell growth medium comprising:
- a first stimulant of cell proliferation (e.g., a first cytokine that stimulates T cell proliferation);
- a second stimulant of cell proliferation (e.g., a second cytokine that stimulates T cell proliferation); and
- an extracellular modulator of cell metabolism (e.g., T cell metabolism).

The immune cells of the disclosure can be activated and expanded, either prior to or after genetic modification of the immune cells, using methods as generally known and as generally described herein. In some embodiments, immune cells (e.g., T cells) are activated and expanded prior to genetic modification of the immune cells. In some embodiments, immune cells (e.g., T cells) are activated and expanded after genetic modification of the immune cells (e.g., engineered immune cells, including those described herein).

Accordingly, conditions appropriate for T cell expansion include an appropriate medium (e.g., Minimal Essential Media or RPMI Media 1640 or, X-vivo 15, (Lonza)) that comprise the first and second stimulants of cell proliferation (e.g., IL-7 and IL-15) as well as an extracellular modulator of cell metabolism (e.g., extracellular potassium) and which can contain further factors necessary for proliferation and viability, including serum (e.g., fetal bovine or human serum), IL-2, insulin, IFN-γ, IL-4, IL-7, GM-CSF, IL-10, IL-2, IL-15, TGFbeta, and TNF, or any other additives for the growth of cells known to the skilled artisan. In some embodiments, the medium for T cell culture does not include exogenous IL-2. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells (e.g., IL-7 and/or IL-15). Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times can exhibit different characteristics.

Methods described herein can further include contacting cells with an agent that stimulates a CD3 TCR complex and a co-stimulatory molecule on the surface of the T-cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, T cell populations also can be stimulated in vitro by contact with, for example, an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. The anti-CD3 antibody and an anti-CD28 antibody can be disposed on a bead or plate or other substrate.

In some embodiments, the cells of the disclosure can be expanded by co-culturing with tissue or cells. The cells can also be expanded in vivo, for example in the subject's blood after administering the cell into the subject.

In particular, cell growth media and methods of use thereof can be particularly useful in the manufacture of T cells, including CAR-T cells such as allogeneic CAR-T cells.

a. Stimulants of Cell Proliferation

In some embodiments, a first and second stimulant are selected from: an agent that stimulates a CD3 TCR complex; an anti-CD3 antibody, or antigen-binding fragment thereof; an anti-CD2 antibody, or antigen-binding fragment thereof; a protein kinase C activator; or a growth factor (e.g., a T cell growth factor), or any combinations thereof.

In some embodiments, a stimulant of immune cells (e.g., T cells or engineered immune cells) is an agent that stimulates a CD3 TCR complex and a co-stimulatory molecule on the surface of the T-cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, a stimulant of immune cells (e.g., T cells or engineered immune cells) is an anti-CD3 antibody, or antigen-binding fragment thereof, or an anti-CD2 antibody immobilized on a surface, or a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. The anti-CD3 antibody and an anti-CD28 antibody can be disposed on a bead or plate or other substrate.

In some embodiments, a stimulant of cells is a growth factor. In some embodiments, a stimulant of cells is a T cell growth factor. In some embodiments, a T cell growth factor is a cytokine. In some embodiments, a first stimulant is a first cytokine, and a second stimulant is a second cytokine. In some embodiments, a cytokine is an interleukin (e.g., IL-2, IL-4, IL-7, IL-10, IL-12, or IL-15). In some embodiments, a first stimulant and a second stimulant are selected from the group consisting of IL-4, IL-7, IL-10, IL-12, and IL-15.

In some embodiments, a first stimulant is IL-7, and a second stimulant is IL-15.

In some embodiments, a cell growth medium excludes IL-2 (e.g., a cell growth medium excludes exogenous IL-2, and IL-2 is not present in a cell growth medium as a first stimulant and/or a second stimulant).

In some embodiments, the amounts used of a first and a second stimulant are described in concentrations (e.g., using IU/mL). Accordingly, a "concentration ratio of x:y" can be used to describe the ratio of the concentration of a first stimulant (e.g., x IU/mL of IL-7) to the concentration of a second stimulant (e.g., y IU/mL of IL-15).

In some embodiments, a first stimulant (e.g., a first cytokine such as IL-7) and a second stimulant (e.g., a second cytokine such as IL-15) are present in a concentration ratio of about 10000:1 to about 1:10000, about 1000:1 to about 1:1000, about 100:1 to about 1:100, or about 10:1 to about 1:10.

In some embodiments, a first stimulant (e.g., a first cytokine such as IL-7) is present in an amount that is greater than a second stimulant (e.g., a second cytokine such as IL-15). In some embodiments, a first stimulant (e.g., a first cytokine such as IL-7) and a second stimulant (e.g., a second cytokine such as IL-15) are present in a concentration ratio of about 1000:1 to about 10:1, about 900:1 to about 10:1, about 800:1 to about 10:1, about 700:1 to about 10:1, about 600:1 to about 10:1, about 500:1 to about 10:1, about 400:1 to about 10:1, about 300:1 to about 10:1, about 250:1 to about 10:1, about 200:1 to about 10:1, about 150:1 to about 10:1, or about 100:1 to about 4:1. In some embodiments, a first stimulant (e.g., a first cytokine such as IL-7) and a second stimulant (e.g., a second cytokine such as IL-15) are present in a concentration ratio of about 1000:1 to about 50:1, about 900:1 to about 50:1, about 800:1 to about 50:1, about 700:1 to about 50:1, about 600:1 to about 50:1, about 500:1 to about 50:1, about 400:1 to about 50:1, about 300:1 to about 50:1, about 250:1 to about 50:1, about 200:1 to about 50:1, about 150:1 to about 50:1, or about 100:1 to about 50:1. In some embodiments, a first stimulant (e.g., a first cytokine such as IL-7) and a second stimulant (e.g., a second cytokine such as IL-15) are present in a concentration ratio of about 200:1 to about 10:1, about 150:1 to about 10:1, about 125:1 to about 10:1, or about 100:1 to about 4:1. In some embodiments, a first stimulant (e.g., a first cytokine such as IL-7) and a second stimulant (e.g., a second cytokine such as IL-15) are present in a concentration ratio of about 100:1. In some embodiments, a first stimulant (e.g., a first cytokine such as IL-7) and a second stimulant (e.g., a second cytokine such as IL-15) are present in a concentration ratio of about 5:1, about 6:1 or about 7.1. In some embodiments, a first stimulant (e.g., a first cytokine such as IL-7) and a second stimulant (e.g., a second cytokine such as IL-15) are present in a concentration ratio of 6.25:1.

In some embodiments, a first stimulant (e.g., a first cytokine such as IL-7) is present in a concentration that is about 100 IU/mL to about 20,000 IU/mL. In some embodiments, a second stimulant (e.g., a second cytokine such as IL-15) is present in a concentration that is about 1 IU/mL to about 200 IU/mL.

In some embodiments, a first stimulant (e.g., a first cytokine such as IL-7) is present in a concentration that is about 100 IU/mL to about 10,000 IU/mL. In some embodiments, a second stimulant (e.g., a second cytokine such as IL-15) is present in a concentration that is about 1 IU/mL to about 100 IU/mL.

In some embodiments, a first stimulant (e.g., a first cytokine such as IL-7) is present in a concentration that is about 100 IU/mL to about 1,000 IU/mL, about 300 IU/mL to about 5,000 IU/mL, or about 3,000 IU/mL. In some embodiments, a first stimulant (e.g., a first cytokine such as IL-7) is present in a concentration that is about 3,000 IU/mL or about 5,000 IU/mL.

In some embodiments, a first stimulant (e.g., a first cytokine such as IL-7) is present in a concentration that is about 2500 IU/mL to about 7500 IU/mL. In some embodiments, a second stimulant (e.g., a second cytokine such as IL-15) is present in a concentration that is about 25 IU/mL to about 75 IU/mL.

In some embodiments, a first stimulant (e.g., a first cytokine such as IL-7) is present in a concentration that is about 4000 IU/mL to about 6000 IU/mL. In some embodiments, a second stimulant (e.g., a second cytokine such as IL-15) is present in a concentration that is about 40 IU/mL to about 60 IU/mL. In some embodiments, a second stimulant (e.g., a second cytokine such as IL-15) is present in a concentration that is about 25 IU/mL to about 100 IU/mL or about 50 IU/mL.

In some embodiments, a first stimulant (e.g., a first cytokine such as IL-7) is present in a concentration that is about 5000 IU/mL. In some embodiments, a second stimulant (e.g., a second cytokine such as IL-15) is present in a concentration that is about 50 IU/mL.

In some embodiments, immune cells (e.g., T cells such as genetically modified T cells) are contacted with a first stimulant (e.g., a first cytokine such as IL-7) and a second stimulant (e.g., a second cytokine such as IL-15) once every about one day, two days, three days, four days, five days, six days, seven days, or eight days. In some embodiments, immune cells (e.g., T cells such as genetically modified T cells) are contacted with a first stimulant (e.g., a first cytokine such as IL-7) and a second stimulant (e.g., a second cytokine such as IL-15) once every about one week. In some embodiments, immune cells (e.g., T cells such as genetically modified T cells) are contacted with a first stimulant (e.g., a first cytokine such as IL-7) and a second stimulant (e.g., a second cytokine such as IL-15) one time, two times, three times, four times, five times, six times, seven times, or eight times during an expansion process that lasts about one day, two days, three days, four days, five days, six days, seven days (e.g., about one week), about two weeks, about three weeks, or about four weeks. In some embodiments, immune cells (e.g., T cells such as genetically modified T cells) are contacted with a first stimulant (e.g., a first cytokine such as IL-7) and a second stimulant (e.g., a second cytokine such as IL-15) for about two weeks.

b. Extracellular Modulators of Cell Metabolism

In some embodiments, a cell growth medium further comprises an extracellular modulator of cell metabolism in addition to a first stimulant (e.g., a first cytokine such as IL-7) and a second stimulant (e.g., a second cytokine such as IL-15) as described herein.

In some embodiments, an extracellular modulator is extracellular potassium ($K^+$). In some embodiments, extracellular potassium is present in a concentration that is about 4 mM to about 50 mM, about 4 mM to about 40 mM, about 4 mM to about 30 mM, about 10 mM to about 40 mM, about 10 mM to about 30 mM, about 15 mM to about 40 mM, about 15 mM to about 35 mM, about 15 mM to about 30 mM, or about 20 mM to about 30 mM. In some embodiments, extracellular potassium is present in a concentration that is about 10 mM to about 30 mM, or about 20 mM to about 30 mM.

In some embodiments, extracellular potassium is present in a concentration that is about 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, or 30 mM.

In some embodiments, extracellular potassium is present in a concentration that is greater than about 15 mM. In some embodiments, extracellular potassium is present in a concentration that is greater than or equal to about 20 mM. In some embodiments, extracellular potassium is present in a concentration that is about 20 mM, 21 mM, 22 mM, 23 mM, 24 mM, 25 mM, 26 mM, 27 mM, 28 mM, 29 mM, or 30 mM.

In some embodiments, extracellular potassium is present in a concentration that is no less than about 10 mM. In some embodiments, extracellular potassium is present in a concentration that is no less than about 20 mM. In some embodiments, extracellular potassium is present in a concentration that is no more than about 30 mM. In some embodiments, extracellular potassium is present in a concentration that is about 25 mM.

In some embodiments, extracellular potassium is provided as KCl.

c. Additional Features and Components of Cell Growth Media

A cell growth medium as described herein (e.g., a cell growth medium comprising a first stimulant that is IL-7, a second stimulant that is IL-15, and an extracellular modulator that is extracellular potassium) can be used in various methods for activating and expanding T cells that are known in the art and are described, for example, in U.S. Pat. Nos. 6,905,874; 6,867,041; 6,797,514; and PCT WO2012/079000, the contents of which are hereby incorporated by reference in their entirety.

In some embodiments, a method further comprises contacting PBMC or isolated T cells with a further stimulatory molecule and a costimulatory molecule, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is the Dynabeads® system, a CD3/CD28 activator/stimulator system for physiological activation of human T cells. In other embodiments, the T cells can be activated and stimulated to proliferate with feeder cells and appropriate antibodies and still other cytokines (e.g., in addition to IL-7 and IL-15) using methods such as those described in U.S. Pat. Nos. 6,040,177; 5,827,642; and WO2012129514, the contents of which are hereby incorporated by reference in their entirety. In some embodiments, cell growth media and methods of use thereof exclude exogenous IL-2 as a T cell growth factor.

Other conditions appropriate for T cell culture include an appropriate media (e.g., Minimal Essential Media or RPMI Media 1640 or, X-Vivo™ medium (Lonza)) that can contain additional factors to, e.g., the first and the second stimulants for cell proliferation, for proliferation and viability, including serum (e.g., fetal bovine or human serum), insulin, IFN-γ, GM-CSF, TGFβ, and TNF, or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo™ 10, X-Vivo™ 15 and X-Vivo™ 20, OpTmizer™, can comprise added amino acids, sodium pyruvate, and/or vitamins, and can be either serum-free or supplemented with an appropriate amount of serum (or plasma) and/or a defined set of hormones. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times can exhibit different characteristics In some embodiments, the cells of the disclosure can be expanded by co-culturing with tissue or cells. The cells can also be expanded in vivo, for example in the subject's blood after administering the cell into the subject.

In some embodiments, a cell growth medium is serum-containing. In some embodiments, a cell growth medium is serum-free. In some embodiments, a cell growth medium is xeno-free. In some embodiments, a cell growth medium is chemically-defined.

d Cell Proliferation

In some embodiments, culturing of cells (including immune cells such as T cells) for in vitro expansion using a cell growth medium described herein (e.g., a cell growth medium comprising a first stimulant that is IL-7, a second stimulant that is IL-15, and an extracellular modulator that is extracellular potassium) or any of the methods described herein is of a duration that is about one day, two days, three days, four days, five days, six days, seven days (e.g., about one week), about two weeks, about three weeks, or about four weeks. In some embodiments, a duration is about one week to about three weeks or about one week to about two weeks (e.g., about 7-15 days or about 10-14 days).

In some embodiments, a cell growth medium described herein (e.g., a cell growth medium comprising a first stimulant that is IL-7, a second stimulant that is IL-15, and an extracellular modulator that is extracellular potassium) or any of the methods described herein results in cell expansion that is at about 10- to about 10000-fold as measured over about a period of about one week to about three weeks. In some embodiments, cell expansion of about 100- to about 1000-fold is observed over about 7-15 days (e.g., over about 10-14 days or over about 2 weeks). In some embodiments, cell expansion of at least about 100-fold is observed over about 7-15 days (e.g., over about 10-14 days or over about 2 weeks). In some embodiments, cell expansion of at least about 200-fold is observed over about 7-15 days (e.g., over about 10-14 days or over about 2 weeks).

In some embodiments, a cell growth medium described herein (e.g., a cell growth medium comprising a first stimulant that is IL-7, a second stimulant that is IL-15, and an extracellular modulator that is extracellular potassium) or any of the methods for cell expansion results in a cell count of at least about $50 \times 10^6$ to about $100 \times 10^6$ over a period of about 8-16 days. In some embodiments, a cell count is of at least about $100 \times 10^6$ over a period of about 10-14 days (e.g., at least about $100 \times 10^6$, about $125 \times 10^6$, about $150 \times 10^6$, or about $100 \times 10^6$ over a period of about 10-14 days).

e. Cell Phenotypes

In some embodiments, a cell growth medium described herein (e.g., a cell growth medium comprising a first stimulant that is IL-7, a second stimulant that is IL-15, and an extracellular modulator that is extracellular potassium) or any method of use thereof produces a desirable phenotype for the production of engineered immune cells.

In some embodiments, a T cell growth medium described herein (e.g., a cell growth medium comprising a first stimulant that is IL-7, a second stimulant that is IL-15, and an extracellular modulator that is extracellular potassium) or any method of use thereof produces a population of T cells (e.g., genetically modified T cells) enriched in $T_{CM}$ and $T_{SCM}$ cells.

In some embodiments, a population of T cells (e.g., genetically modified T cells) enriched in $T_{CM}$ and/or $T_{SCM}$ cells comprises at least about 60%, 65%, 70%, 75%, or 80% combined $T_{CM}$ and $T_{SCM}$ cells. In some embodiments, a population of T cells enriched in $T_{CM}$ and/or $T_{SCM}$ cells comprises at least about 70% combined $T_{CM}$ and $T_{SCM}$ cells. In some embodiments, a population of T cells (e.g., genetically modified T cells) enriched in $T_{CM}$ and $T_{SCM}$ cells comprises at least about 75% combined $T_{CM}$ and/or $T_{SCM}$ cells.

In some embodiments, a population of T cells (e.g., genetically modified T cells) enriched in $T_{CM}$ and/or $T_{SCM}$ cells comprises at least about 20%, 25%, 30%, 35%, 40%, 45%, 50%, 55%, or 60% $T_{SCM}$ cells. In some embodiments, a population of T cells enriched in $T_{CM}$ and/or $T_{SCM}$ cells comprises at least about 30%, 35%, 40%, or 45% $T_{SCM}$ cells.

4. Manufacture of Engineered Immune Cells (Including CAR T Cells)

Provided herein are methods of using cell growth media described herein for manufacture of immune cells (including engineered immune cells such as CAR T cells).

A variety of known techniques can be utilized in making the polynucleotides, polypeptides, vectors, antigen binding domains, immune cells, compositions, and the like according to the disclosure.

Prior to the in vitro manipulation or genetic modification of the immune cells described herein, the cells can be obtained from a subject. Cells expressing a CAR can be derived from an allogeneic or autologous process.

a. Source Material

Cell growth media described herein (e.g., comprising IL-7+IL-15 and increased extracellular potassium) can be used to culture various cells, including for the in vitro expansion of various immune cells (e.g., genetically modified T cells). Exemplary cells are described herein.

In some embodiments, the immune cells comprise T cells. T cells can be obtained from a number of sources, including peripheral blood mononuclear cells (PBMCs), bone marrow, lymph nodes tissue, cord blood, thymus tissue, tissue from a site of infection, ascites, pleural effusion, spleen tissue, and tumors. In certain some embodiments, T cells can be obtained from a volume of blood collected from the subject using any number of techniques known to the skilled person, such as FICOLL™ separation.

Cells can be obtained from the circulating blood of an individual by apheresis. The apheresis product typically contains lymphocytes, including T cells, monocytes, granulocytes, B cells, other nucleated white blood cells, red blood cells, and platelets. In certain some embodiments, the cells collected by apheresis can be washed to remove the plasma fraction, and then placed in an appropriate buffer or media for subsequent processing.

In certain some embodiments, T cells are isolated from PBMCs by lysing the red blood cells and depleting the monocytes, for example, using centrifugation through a PERCOLL™ gradient. A specific subpopulation of T cells, (e.g., CD28+, CD4+, CD45RA−, and CD45RO+ T cells or CD28+, CD4+, CD8+, CD45RA−, CD45RO+, and CD62L+ T cells) can be further isolated by positive or negative selection techniques known in the art. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting can also be used to isolate cell populations of interest for use in the present disclosure.

PBMCs can be used directly for genetic modification with the immune cells (such as CARs or TCRs) using methods as described herein. In certain some embodiments, after isolating the PBMCs, T lymphocytes can be further isolated and both cytotoxic and helper T lymphocytes can be sorted into naive, memory, and effector T cell subpopulations either before or after genetic modification and/or expansion.

In some embodiments, CD8+ cells are further sorted into naive, stem cell memory, central memory, and effector cells by identifying cell surface antigens that are associated with each of these types of CD8+ cells. In some embodiments, the expression of phenotypic markers of central memory T cells include CD27, CD45RA, CD45RO, CD62L, CCR7, CD28, CD3, and CD127 and are negative for granzyme B. In some embodiments, stem cell memory T cells are CD45RO−, CD62L+, CD8+ T cells. In some embodiments, central memory T cells are CD45RO+, CD62L+, CD8+ T cells. In some embodiments, effector T cells are negative for CD62L, CCR7, CD28, and CD127, and positive for granzyme B and perforin. In certain some embodiments, CD4+ T cells are further sorted into subpopulations. For example, CD4+ T helper cells can be sorted into naive, central memory, and effector cells by identifying cell populations that have cell surface antigens.

b. Stem Cell Derived Immune Cells

In some embodiments, the immune cells can be derived from embryonic stem (ES) or induced pluripotent stem (iPS) cells. Suitable HSCs, mesenchymal, iPS cells and other types of stem cells can be cultivated immortal cell lines or isolated directly from a patient. Various methods for isolating, developing, and/or cultivating stem cells are known in the art and can be used to practice the present disclosure.

In some embodiments, the immune cell is an induced pluripotent stem cell (iPSC) derived from a reprogrammed T-cell. In some embodiments, the source material can be an induced pluripotent stem cell (iPSC) derived from a T cell or a non-T cell. The source material can be an embryonic stem cell. The source material can be a B cell, or any other cell from peripheral blood mononuclear cell isolates, hematopoietic progenitor, hematopoietic stem cell, mesenchymal stem cell, adipose stem cell, or any other somatic cell type.

c. Genetic Modification of Isolated Cells

The immune cells, such as T cells, can be genetically modified following isolation using known methods, or the immune cells can be activated and expanded (or differentiated in the case of progenitors) in vitro prior to being genetically modified. In some embodiments, the isolated immune cells are genetically modified to reduce or eliminate expression of endogenous TCRα and/or CD52. In some embodiments, the cells are genetically modified using gene editing technology (e.g., CRISPR/Cas9, a zinc finger nuclease (ZFN), a TALEN, a MegaTAL, a meganuclease) to reduce or eliminate expression of endogenous proteins (e.g., TCRα and/or CD52). In another embodiment, the immune cells, such as T cells, are genetically modified with the chimeric antigen receptors described herein (e.g., transduced with a viral vector comprising one or more nucleotide sequences encoding a CAR) and then are activated and/or expanded in vitro.

Certain methods for making the constructs and engineered immune cells of the disclosure are described in PCT application PCT/US15/14520, the contents of which are hereby incorporated by reference in their entirety.

It will be appreciated that PBMCs can further include other cytotoxic lymphocytes such as NK cells or NKT cells. An expression vector carrying the coding sequence of a chimeric receptor as disclosed herein can be introduced into a population of human donor T cells, NK cells or NKT cells. Successfully transduced T cells that carry the expression vector can be sorted using flow cytometry to isolate CD3 positive T cells and then further propagated to increase the number of these CAR expressing T cells in addition to cell activation using anti-CD3 antibodies and IL-2 or other methods known in the art as described elsewhere herein. Standard procedures are used for cryopreservation of T cells expressing the CAR for storage and/or preparation for use in a human subject. In one embodiment, the in vitro transduction, culture and/or expansion of T cells are performed in the absence of non-human animal derived products such as fetal calf serum and fetal bovine serum.

For cloning of polynucleotides, the vector can be introduced into a host cell (an isolated host cell) to allow replication of the vector itself and thereby amplify the copies of the polynucleotide contained therein. The cloning vectors can contain sequence components generally include, without limitation, an origin of replication, promoter sequences, transcription initiation sequences, enhancer sequences, and selectable markers. These elements can be selected as appropriate by a person of ordinary skill in the art. For example, the origin of replication can be selected to promote autonomous replication of the vector in the host cell.

In certain some embodiments, the present disclosure provides isolated host cells containing the vector provided herein. The host cells containing the vector can be useful in expression or cloning of the polynucleotide contained in the vector. Suitable host cells can include, without limitation, prokaryotic cells, fungal cells, yeast cells, or higher eukaryotic cells such as mammalian cells, particularly human cells.

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art. In a further embodiment, a mixture of different expression vectors can be used in genetically modifying a donor population of immune effector cells wherein each vector encodes a different CAR as disclosed herein. The resulting transduced immune effector cells form a mixed population of engineered cells, with a proportion of the engineered cells expressing more than one different CARs.

In one embodiment, the disclosure provides a method of storing genetically engineered cells expressing CARs or TCRs. This involves cryopreserving the immune cells such that the cells remain viable upon thawing. A fraction of the immune cells expressing the CARs can be cryopreserved by methods known in the art to provide a permanent source of such cells for the future treatment of patients afflicted with a malignancy. When needed, the cryopreserved transformed immune cells can be thawed, grown and expanded for more such cells.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

d. Allogeneic CAR T (ALLOCAR T™) Cells

The process for manufacturing allogeneic CAR T therapy, or AlloCARs™ involves harvesting healthy, selected, screened and tested T cells from healthy donors. Next, the T cells are engineered to express CARs, which recognize certain cell surface proteins that are expressed in hematologic or solid tumors. Allogeneic T cells are gene editing to reduce the risk of graft versus host disease (GvHD) and to prevent allogeneic rejection. A T cell receptor gene (e.g., TCRα, TCRβ) is knocked out to avoid GvHD. The CD52 gene can be knocked out to render the CAR T product resistant to anti-CD52 antibody treatment. Anti-CD52 antibody treatment can therefore be used to suppress the host immune system and allow the CAR T to stay engrafted to achieve full therapeutic impact. The engineered T cells then undergo a purification step and are ultimately cryopreserved in vials for delivery to patients.

e. Autologous CAR T (AUTOCAR T™) Cells

Autologous chimeric antigen receptor (CAR) T cell therapy, involves collecting a patient's own cells (e.g., white blood cells, including T cells) and genetically engineering the T cells to express CARs that recognize target expressed on the cell surface of one or more specific cancer cells and kill cancer cells. The engineered cells are then cryopreserved and subsequently administered to the patient.

5. Pharmaceutical Compositions and Therapy

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

In embodiments, desired treatment amounts of cells in the composition are generally at least 2 cells (for example, at least 1 CD8+ central or stem cell memory T cell and at least 1 CD4+ helper T cell subset; or two or more CD8+ central or stem cell memory T cell; or two or more CD4+ helper T cell subset) or is more typically greater than $10^2$ cells, and up to and including $10^6$, up to and including 10', $10^8$ or $10^9$ cells and can be more than $10^{10}$ cells. The number of cells will depend upon the desired use for which the composition is intended, and the type of cells included therein. The density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$ $10^{10}$, $10^{11}$ or $10^{12}$ cells. In some aspects of the present disclosure, particularly since all the infused cells will be redirected to a particular target antigen, lower numbers of cells, in the range of about $10^5$/kilogram or about $10^6$/kilogram ($10^6$-$10^{11}$ per patient) can be administered. CAR treatments can be administered multiple times at dosages within these ranges. The cells can be autologous, allogeneic, or heterologous to the patient undergoing therapy.

The CAR expressing cell populations of the present disclosure can be administered either alone, or as a pharmaceutical composition in combination with diluents and/or with other components such as IL-2 or other cytokines or cell populations. Pharmaceutical compositions of the present disclosure can comprise a CAR or TCR expressing cell population, such as T cells, as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

The pharmaceutical compositions (solutions, suspensions or the like), can include one or more of the following: sterile diluents such as water for injection, saline solution, preferably physiological saline, Ringer's solution, isotonic sodium chloride, fixed oils such as synthetic mono- or diglycerides which can serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic. An injectable pharmaceutical composition is preferably sterile.

6. Methods of Treatment

The disclosure comprises methods for treating or preventing a disease (e.g., cancer) in a patient, comprising administering to a patient in need thereof an effective amount of at least one CAR, or immune-cell comprising a CAR disclosed herein.

Methods are provided for treating diseases or disorders, including cancer. In some embodiments, the disclosure relates to creating a T cell-mediated immune response in a subject, comprising administering an effective amount of the engineered immune cells of the present application to the subject. In some embodiments, the T cell-mediated immune response is directed against a target cell or cells. In some embodiments, the engineered immune cell comprises a chimeric antigen receptor (CAR). In some embodiments, the target cell is a tumor cell. In some aspects, the disclosure comprises a method for treating or preventing a malignancy, said method comprising administering to a subject in need thereof an effective amount of at least one isolated antigen binding domain described herein. In some aspects, the disclosure comprises a method for treating or preventing a malignancy, said method comprising administering to a subject in need thereof an effective amount of at least one immune cell, wherein the immune cell comprises at least one chimeric antigen receptor, T cell receptor, and/or isolated antigen binding domain as described herein. The CAR containing immune cells of the disclosure can be used to treat malignancies involving aberrant expression of biomarkers. In some embodiments, CAR containing immune cells of the disclosure can be used to treat small cell lung cancer, melanoma, low grade gliomas, glioblastoma, medullary thyroid cancer, carcinoids, dispersed neuroendocrine tumors in the pancreas, bladder and prostate, testicular cancer, and lung adenocarcinomas with neuroendocrine features. In exemplary embodiments, the CAR containing immune cells, e.g., CAR-T cells of the disclosure are used to treat small cell lung cancer.

Also provided are methods for reducing the size of a tumor in a subject, comprising administering to the subject an engineered cell of the present disclosure to the subject, wherein the cell comprises a chimeric antigen receptor comprising an antigen binding domain and binds to an antigen on the tumor.

In some embodiments, the subject has a solid tumor, or a blood malignancy such as lymphoma or leukemia. In some embodiments, the engineered cell is delivered to a tumor bed. In some embodiments, the cancer is present in the bone marrow of the subject. In some embodiments, the engineered cells are autologous immune cells, e.g., autologous T cells. In some embodiments, the engineered cells are allogeneic immune cells, e.g., allogeneic T cells. In some embodiments, the engineered cells are heterologous immune cells, e.g., heterologous T cells. In some embodiments, the engineered cells of the present application are transfected or transduced in vivo. In other embodiments, the engineered cells are transfected or transduced ex vivo. As used herein, the term "in vitro cell" refers to any cell which is cultured ex vivo.

A "therapeutically effective amount," "effective dose," "effective amount," or "therapeutically effective dosage" of a therapeutic agent, e.g., engineered CART cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. The term "prevent" does not require the 100% elimination of the possibility of an event. Rather, it denotes that the likelihood of the occurrence of the event has been reduced in the presence of the compound or method.

Desired treatment amounts of cells in the composition is generally at least 2 cells (for example, at least 1 CD8+ central memory T cell and at least 1 CD4+ helper T cell subset) or is more typically greater than $10^2$ cells, and up to $10^6$, up to and including $10^8$ or $10^9$ cells and can be more than $10^{10}$ cells. The number of cells will depend upon the desired use for which the composition is intended, and the type of cells included therein. The density of the desired cells is typically greater than $10^6$ cells/ml and generally is greater than $10^7$ cells/ml, generally 108 cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present disclosure, particularly since all the infused cells will be redirected to a particular target antigen, lower numbers of cells, in the range of $10^6$/kilogram ($10^6$-$10^{11}$ per patient) can be administered. CAR treatments can be administered multiple times at dosages within these ranges. The cells can be autologous, allogeneic, or heterologous to the patient undergoing therapy.

In some embodiments, the therapeutically effective amount of the CAR T cells is about $1\times10^5$ cells/kg, about $2\times10^5$ cells/kg, about $3\times10^5$ cells/kg, about $4\times10^5$ cells/kg, about $5\times10^5$ cells/kg, about $6\times10^5$ cells/kg, about $7\times10^5$ cells/kg, about $8\times10^5$ cells/kg, about $9\times10^5$ cells/kg, $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

In some embodiments, target doses for CAR+/CAR−T+/TCR+ cells range from $1\times10^6$-$2\times10^8$ cells/kg, for example $2\times10^6$ cells/kg. It will be appreciated that doses above and below this range can be appropriate for certain subjects, and appropriate dose levels can be determined by the healthcare provider as needed. Additionally, multiple doses of cells can be provided in accordance with the disclosure.

In some aspects, the disclosure comprises a pharmaceutical composition comprising at least one antigen binding domain as described herein and a pharmaceutically acceptable excipient. In some embodiments, the pharmaceutical composition further comprises an additional active agent.

The CAR expressing cell populations of the present disclosure can be administered either alone, or as a pharmaceutical composition in combination with diluents and/or with other components such as IL-2 or other cytokines or cell populations. Pharmaceutical compositions of the present disclosure can comprise a CAR or TCR expressing cell population, such as T cells, as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

The pharmaceutical compositions (solutions, suspensions or the like), can include one or more of the following: sterile diluents such as water for injection, saline solution, preferably physiological saline, Ringer's solution, isotonic sodium chloride, fixed oils such as synthetic mono- or diglycerides which can serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic. An injectable pharmaceutical composition is preferably sterile.

In some embodiments, upon administration to a patient, engineered immune cells expressing at their cell surface any one of the antigen-specific CARs described herein can reduce, kill or lyse endogenous antigen-expressing cells of the patient. In one embodiment, a percentage reduction or lysis of antigen-expressing endogenous cells or cells of a cell line expressing an antigen by engineered immune cells expressing any one of an antigen-specific CARs described herein is at least about or greater than 10%, 15%, 20%, 25%, 30%, 35%, 40%, 45%, 50%, 55%, 60%, 65%, 70%, 75%, 80%, 85%, 90%, or 95%. In one embodiment, a percentage reduction or lysis of antigen-expressing endogenous cells or cells of a cell line expressing an antigen by engineered immune cells expressing antigen-specific CARs is about 5% to about 95%, about 10% to about 95%, about 10% to about 90%, about 10% to about 80%, about 10% to about 70%, about 10% to about 60%, about 10% to about 50%, about 10% to about 40%, about 20% to about 90%, about 20% to about 80%, about 20% to about 70%, about 20% to about 60%, about 20% to about 50%, about 25% to about 75%, or about 25% to about 60%. In one embodiment, the endogenous antigen-expressing cells are endogenous antigen-expressing bone marrow cells.

In one embodiment, the percent reduction or lysis of target cells, e.g., a cell line expressing an antigen, by engineered immune cells expressing at their cell surface membrane an antigen-specific CAR of the disclosure can be measured using the assay disclosed herein.

The methods can further comprise administering one or more chemotherapeutic agent. In certain some embodiments, the chemotherapeutic agent is a lymphodepleting (preconditioning) chemotherapeutic. For example, methods of conditioning a patient in need of a T cell therapy comprising administering to the patient specified beneficial doses of cyclophosphamide (between 200 mg/m$^2$/day and 2000 mg/m$^2$/day, about 100 mg/m$^2$/day and about 2000 mg/m$^2$/day; e.g., about 100 mg/m$^2$/day, about 200 mg/m$^2$/day, about 300 mg/m$^2$/day, about 400 mg/m$^2$/day, about 500 mg/m$^2$/day, about 600 mg/m$^2$/day, about 700 mg/m$^2$/day, about 800 mg/m$^2$/day, about 900 mg/m$^2$/day, about 1000 mg/m$^2$/day, about 1500 mg/m$^2$/day or about 2000 mg/m$^2$/day) and specified doses of fludarabine (between 20 mg/m$^2$/day and 900 mg/m$^2$/day, between about 10 mg/m$^2$/day and about 900 mg/m$^2$/day; e.g., about 10 mg/m$^2$/day, about 20 mg/m$^2$/day, about 30 mg/m$^2$/day, about 40 mg/m$^2$/day, about 40 mg/m$^2$/day, about 50 mg/m$^2$/day, about 60 mg/m$^2$/day, about 70 mg/m$^2$/day, about 80 mg/m$^2$/day, about 90 mg/m$^2$/day, about 100 mg/m$^2$/day, about 500 mg/m$^2$/day or about 900 mg/m$^2$/day). A preferred dose regimen involves treating a patient comprising administering daily to the patient about 300 mg/m$^2$/day of cyclophosphamide and about 30 mg/m$^2$/day of fludarabine for three days prior to administration of a therapeutically effective amount of engineered T cells to the patient.

In some embodiments, lymphodepletion further comprises administration of a CD52 antibody. In some embodiments, the CD52 antibody is administered at a dose of about 13 mg/day IV.

In other embodiments, the antigen binding domain, transduced (or otherwise engineered) cells and the chemotherapeutic agent are administered each in an amount effective to treat the disease or condition in the subject.

In certain some embodiments, compositions comprising CAR-expressing immune effector cells disclosed herein can be administered in conjunction with any number of chemotherapeutic agents, which can be administered in any order. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2', 2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RF S2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell, polypeptide, or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell, polypeptide, or nucleic acid. In other embodiments, the chemotherapeutic agent is administered at least 1 month before administering the cell, polypeptide, or nucleic acid. In some embodiments, the methods further comprise administering two or more chemotherapeutic agents.

A variety of additional therapeutic agents can be used in conjunction with the compositions described herein. For example, potentially useful additional therapeutic agents include PD-1 inhibitors such as nivolumab (Opdivo®), pembrolizumab (Keytruda®), pembrolizumab, pidilizumab, and atezolizumab.

Additional therapeutic agents suitable for use in combination with the disclosure include, but are not limited to, ibrutinib (Imbruvica®), ofatumumab(Arzerra®, rituximab (Rituxan®), bevacizumab (Avastin®), trastuzumab (Herceptin®), trastuzumab emtansine (KADCYLA®, imatinib (Gleevec®), cetuximab (Erbitux®, panitumumab) (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept,adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In some embodiments, the composition comprising CAR-containing immune cells can be administered with a therapeutic regimen to prevent cytokine release syndrome (CRS) or neurotoxicity. The therapeutic regimen to prevent cytokine release syndrome (CRS) or neurotoxicity can include lenzilumab, tocilizumab, atrial natriuretic peptide (ANP), anakinra, iNOS inhibitors (e.g., L-NIL or 1400W). In additional embodiments, the composition comprising CAR-containing immune cells can be administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain some embodiments, the compositions described herein are administered in conjunction with a cytokine. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, IL-21 a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

7. Methods of Sorting and Depletion

In some embodiments, provided are methods for in vitro sorting of a population of immune cells, wherein a subset of the population of immune cells comprises engineered immune cells expressing an antigen-specific CARs comprising epitopes specific for monoclonal antibodies (e.g., exemplary mimotope sequences). The method comprises contacting the population of immune cells with a monoclonal antibody specific for the epitopes and selecting the immune cells that bind to the monoclonal antibody to obtain a population of cells enriched in engineered immune cells expressing an antigen-specific CAR.

In some embodiments, said monoclonal antibody specific for said epitope is optionally conjugated to a fluorophore. In this embodiment, the step of selecting the cells that bind to the monoclonal antibody can be done by Fluorescence Activated Cell Sorting (FACS).

In some embodiments, said monoclonal antibody specific for said epitope is optionally conjugated to a magnetic particle. In this embodiment, the step of selecting the cells that bind to the monoclonal antibody can be done by Magnetic Activated Cell Sorting (MACS).

In some embodiments, the mAb used in the method for sorting immune cells expressing the CAR is chosen from alemtuzumab, ibritumomab tiuxetan, muromonab-CD3, tositumomab, abciximab, basiliximab, brentuximab vedotin, cetuximab, infliximab, rituximab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and/or ustekinumab. In some embodiments, said mAb is rituximab. In another embodiment, said mAb is QBEND-10. In another emboidment the mAb binds to TCRα or TCRβ.

In some embodiments, the population CAR-expressing immune cells obtained when using the method for in vitro sorting CAR-expressing immune cells described above, comprises at least 70%, 75%, 80%, 85%, 90%, 95% of CAR-expressing immune cells. In some embodiments, the population of CAR-expressing immune cells obtained when using the method for in vitro sorting CAR-expressing immune cells, comprises at least 85% CAR-expressing immune cells.

In some embodiments, the population of CAR-expressing immune cells obtained when using the method for in vitro sorting CAR-expressing immune cells described above shows increased cytotoxic activity in vitro compared with the initial (non-sorted) cell population. In some embodiments, said cytotoxic activity in vitro is increased by 10%, 20%, 30% or 50%. In some embodiments, the immune cells are T-cells.

In some embodiments, the mAbs are previously bound onto a support or surface. Non-limiting examples of solid support can include a bead, agarose bead, a magnetic bead, a plastic welled plate, a glass welled plate, a ceramic welled plate, a column, or a cell culture bag.

The CAR-expressing immune cells to be administered to the recipient can be enriched in vitro from the source population. Methods of expanding source populations can include selecting cells that express an antigen such as CD34 antigen, using combinations of density centrifugation, immuno-magnetic bead purification, affinity chromatography, and fluorescent activated cell sorting.

Flow cytometry is can be used to quantify specific cell types within a population of cells. In general, flow cytometry is a method for quantitating components or structural features of cells primarily by optical means. Since different cell types can be distinguished by quantitating structural features, flow cytometry and cell sorting can be used to count and sort cells of different phenotypes in a mixture.

A flow cytometry analysis involves two primary steps: 1) labeling selected cell types with one or more labeled markers, and T) determining the number of labeled cells relative to the total number of cells in the population. In some embodiments, the method of labeling cell types includes binding labeled antibodies to markers expressed by the specific cell type. The antibodies can be either directly labeled with a fluorescent compound or indirectly labeled using, for example, a fluorescent-labeled second antibody which recognizes the first antibody.

In some embodiments, the method used for sorting T cells expressing CAR is the Magnetic-Activated Cell Sorting (MACS). Magnetic-activated cell sorting (MACS) is a method for separation of various cell populations depending on their surface antigens (CD molecules) by using superparamagnetic nanoparticles and columns. MACS can be used to obtain a pure cell population. Cells in a single-cell suspension can be magnetically labeled with microbeads. The sample is applied to a column composed of ferromagnetic spheres, which are covered with a cell-friendly coating allowing fast and gentle separation of cells. The unlabeled cells pass through while the magnetically labeled cells are retained within the column. The flow-through can be collected as the unlabeled cell fraction. After a washing step, the column is removed from the separator, and the magnetically labeled cells are eluted from the column.

Detailed protocol for the purification of specific cell population such as T-cell can be found in Basu S et al. (2010). (Basu S, Campbell H M, Dittel B N, Ray A. Purification of specific cell population by fluorescence activated cell sorting (FACS). J Vis Exp. (41): 1546).

In some aspects, the present disclosure provides a method for depleting antigen-specific CAR-expressing immune cells by in vivo depletion. in vivo depletion can include the administration of a treatment (e.g., a molecule that binds an epitope on the CAR) to a mammalian organism aiming to stop the proliferation of the CAR-expressing immune cells by inhibition or elimination.

One aspect of the disclosure is related to a method for in vivo depleting an engineered immune cell expressing a CAR comprising a mAb specific epitope, comprising contacting said engineered immune cell or said CAR-expressing immune cell with at least one epitope-specific mAb. Another aspect of the disclosure relates to a method for in vivo depleting CAR-expressing immune cell which comprises a chimeric scFv (e.g., formed by insertion of a mAb-specific epitope) by contacting said engineered immune cell with epitope-specific antibodies. In some embodiments, the immune cells are T-cells and/or the antibodies are monoclonal.

According to one embodiment, the in vivo depletion of the immune engineered cells is performed on engineered immune cells which has been previously sorted using an in vitro method of the present disclosure. In this case, the same infused mAb can be used. In some embodiments, the mAb-specific antigen is CD20 antigen and the epitope-specific mAb is rituximab. In some embodiments, the disclosure relates to a method for in vivo depleting an engineered immune cell expressing a CAR comprising an mAb-specific epitope (CAR-expressing immune cell) in a patient comprising contacting said CAR-expressing immune cell with at least one epitope-specific mAb In some embodiments, the step of contacting said engineered immune cell or said CAR-expressing immune cell with at least one epitope-specific mAb comprises infusing the patient with an epitope-specific mAb (e.g., rituximab). In some embodiments, the amount of epitope-specific mAb administered to the patient is sufficient to eliminate at least 20%, 30%, 40%, 50%, 60%, 70%, 80% or 90% of the CAR-expressing immune cell in the patient.

In some embodiments, the step of contacting said engineered immune cell or said CAR-expressing immune cell with at least one epitope-specific mAb comprises infusing the patient with 375 mg/m$^2$ of rituximab, once or several times. In some embodiments, the mAb (e.g., rituximab) is administered once weekly.

In some embodiments, when immune cells expressing a CAR comprising an mAb-specific epitope (CAR-expressing immune cells) are depleted in a complement dependent cytotoxicity (CDC) assay using epitope-specific mAb, the amount of viable CAR-expressing immune cells decreases. In some embodiments, the amount of viable CAR-expressing immune cells decreases by at least 10%, 20%, 30%, 40%, 50%, 60%, 70%, 80% or 90%. In some embodiments, said mAb-specific epitope is a CD20 epitope or mimotope and/or the epitope-specific mAb is rituximab.

In certain some embodiments, the in vivo depletion of CAR-engineered immune cells is performed by infusing bi-specific antibodies. By definition, a bispecific monoclonal antibody (BsAb) is an artificial protein that is composed of fragments of two different monoclonal antibodies and consequently binds to two different types of antigen. These BsAbs and their use in immunotherapy have been reviewed in Muller D and Kontermann R. E. (2010) Bispecific Antibodies for Cancer Immunotherapy, BioDrugs 24 (2): 89-98.

According to another particular embodiment, the infused bi-specific mAb is able to bind both the mAb-specific epitope borne on engineered immune cells expressing the chimeric scFv and to a surface antigen on an effector and cytotoxic cell (e.g., immune cells such as lymphocytes, macrophages, dendritic cells, natural killer cells (NK Cell), cytotoxic T lymphocytes (CTL)). By doing so, the depletion of engineered immune cells triggered by the BsAb can occur through antibody-dependent cellular cytotoxicity (ADCC). (Deo Y M, Sundarapandiyan K, Keler T, Wallace P K, and Graziano R F, (2000), Journal of Immunology, 165 (10): 5954-5961]).

In some embodiments, a cytotoxic drug is coupled to the epitope-specific mAbs which can be used to deplete CAR-expressing immune cells. By combining targeting capabilities of monoclonal antibodies with the cancer-killing ability of cytotoxic drugs, antibody-drug conjugate (ADC) allows a sensitive discrimination between healthy and diseased tissue when compared to the use of the drug alone. Market approvals were received for several ADCs; the technology for making them—particularly on linkers—are described in (Payne, G. (2003) Cancer Cell 3:207-212; Trail et al (2003) Cancer Immunol. Immunother. 52:328-337; Syrigos and Epenetos (1999) Anticancer Research 19:605-614; Niculescu-Duvaz and Springer (1997) Adv. Drug Del. Rev. 26:151-172; U.S. Pat. No. 4,975,278).

In some embodiments, the epitope-specific mAb to be infused is conjugated beforehand with a molecule able to promote complement dependent cytotoxicity (CDC). Therefore, the complement system helps or complements the ability of antibodies to clear pathogens from the organism. When stimulated an activation cascade is triggered as a massive amplification of the response and activation of the cell-killing membrane attack complex. Different molecule can be used to conjugate the mAb, such as glycans [Courtois, A, Gac-Breton, S., Berthou, C, Guezennec, J., Bordron, A. and Boisset, C. (2012), Complement dependent cytotoxicity activity of therapeutic antibody fragments can be acquired by immunogenic glycan coupling, Electronic Journal of Biotechnology ISSN: 0717-3458; www.ejbiotechnology.info DOI: 10.2225/vol15-issue5].

8. Kits and Articles of Manufacture

The present disclosure provides kits comprising any of the cultured immune cells or engineered immune cells described herein, and pharmaceutical compositions of the same. In some exemplary embodiments, a kit of the disclosure comprises allogeneic CAR-containing T-cells for administering to a subject.

The present application also provides articles of manufacture comprising any one of the therapeutic compositions or kits described herein. Examples of an article of manufacture include vials (e.g. sealed vials).

Further the instant disclosure provides kits comprising one or more containers comprising a solution of potassium at a desired concentration, and optionally one or more containers comprising a solution comprising one or more cytokines, such as IL-7 or IL-15.

Examples

As shown in the following examples, combinations of cytokine and metabolic modulators conditions and concentrations in T cell expansion media can lead to increased potency of genetically-modified allogeneic cell therapy products. For example, desirable allogeneic CAR T cell phenotypes can be obtained through the use of stimulants of cell proliferation, e.g., IL-7, IL-15, and increased extracellular potassium.

1. Exemplary Protocol for CAR T Cell Production

As described herein, CAR T cells can be produced according to various methods known in the art. An exemplary, standard method is described herein.

To generate CAR-T cells, PBMCs can be purified from buffy coat samples of healthy volunteer using Ficoll gradient density medium (Ficoll Paque PLUS/GE Healthcare Life Sciences). T cells can be purified from PBMCs using a commercially available T cell isolation kit (Miltenyi Biotec, Cat #130-096-535). Alternatively, primary human T cells can be directly purified from Leuko Paks (StemCell Technologies).

To make lentivirus encoding CARs, HEK-293T cells can be plated at 0.4 million cells per mL in 2 mL of DMEM (Gibco) supplemented with 10% FBS (Hyclone or JR Scientific) per well of a 6-well plate on Day 0. On Day 1, the lentivirus can be prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM can be incubated at room temperature for 5 minutes and then added to the DNA mix. The mixture can be incubated at room temperature for 20 minutes and the total volume of 500 uL was slowly added to the sides of the wells containing HEK-293T.

Purified T cells can be activated in a suitable medium. On Day 2, the media from each well of the 6-well plate can be replaced with 2 mL per well of T cell transduction media, i.e., X-Vivo-15 supplemented with 10% FBS. On Day 3, T cells can be re-suspended at 0.5 million cells per mL in 1 mL of T cell transduction media per well of a Grex-24 plate (Wilson Wolf, cat #80192M). The lentiviral supernatants from HEK293T cells can be harvested and passed through a 0.45 micron filter (EMD Millipore) to remove cell debris, and then added to the T cells along with 100 IU/mL human IL-2.

On Day 5, 4.5 mL of T cell expansion media (e.g., comprising IL-7+IL-15 and with or without additional extracellular potassium) can be added to each well of a Grex-24 plate. On Day 9 and Day 13, transduction efficiency can be determined by detecting the percentage of T cells that recognize the desired antigen (e.g., a recombinant antigen) using flow cytometry. Cells were expanded into larger flasks or G-Rex vessels (Wilson Wolf) as needed using T cell expansion media as described herein.

On Day 14, antigen-specific CAR-T cells can be cryopreserved, e.g., by freezing the cells in a medium such as CryoStor® CS5, CryoStor®CS10 or CryoStor® CS2 (BioLife Solutions). Percentage of cells stained with recombinant antigen can be normalized across clones right before cryopreservation.

2. IL-7+15 supplementation

The data in the following examples demonstrate, e.g., the use of a first stimulant and a second stimulant, for instance, IL-7 (5,000 IU/ml) and IL-15 (50 IU/ml), optionally plus increased extracellular potassium (25 mM), can achieve a highly desirable phenotype of allogeneic CART cells, as compared to classical IL-2-based processes.

Figure 1B:
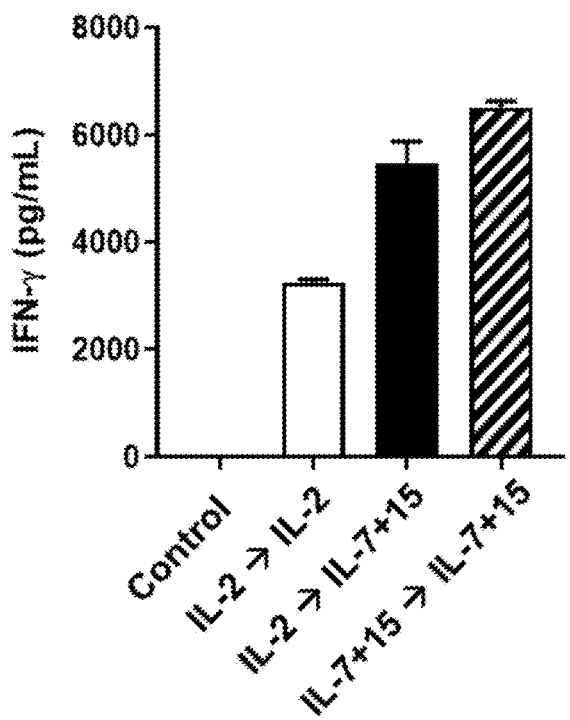
FIG. 1B depicts the cytokine-release capabilities of CD19-specific CART cells upon target cell exposure, where the CAR T cells were prepared using manufacturing processes comprising sequential IL-2 stimulation; IL-2 stimulation followed by IL-7+IL-15 stimulation; and sequential IL-7+IL-15 stimulation.

We first tested IL-7 and IL-15 supplementation in cell culture media in which potassium was kept at the 4 mM baseline level. As shown in FIG. 1A, when benchmarked to an IL-2 based manufacturing process ("IL-2→IL-2"—100 IU/mL IL-2 throughout, fresh IL-2 was added on Day 5), an IL-7+IL-15-based process (either "IL-2→IL-7+15"—100 IU/mL IL-2 until Day 2, on Day 5, 5000 IU/mL IL-7 and 50 IU/mL IL-15 were added, or "IL-7+15→IL-7+15"—5000 IU/mL IL-7 and 50 IU/mL IL-15 throughout with fresh IL-7 and IL-15 added on Day 5) increased the abundance of $T_{SCM}$ (CD62L$^+$CD45RO$^-$) of CD19-specific CAR T cells in the final product. As shown in FIG. 1B, IL-7+15 culturing conditions also increased the cytokine-release capabilities of the CD19-specific CAR T cells upon target cell exposure.

3. Potassium Supplementation and Titration Studies

To further improve the potency of our allogeneic CAR T cells we investigated combining the benefits of IL-7+15 supplementation at the same concentrations as in previous experiments with extracellular nutrients known to modulate T cell metabolism. Extracellular potassium has been shown to be a suppressive mechanism by which the tumor microenvironment (TME) suppresses effector T cells in vivo. On the other hand, increased extracellular potassium during in vitro expansion of adoptive cell therapies (ACT) leads to the preservation of T cells with a younger less-differentiated phenotype.

Figure 2A:
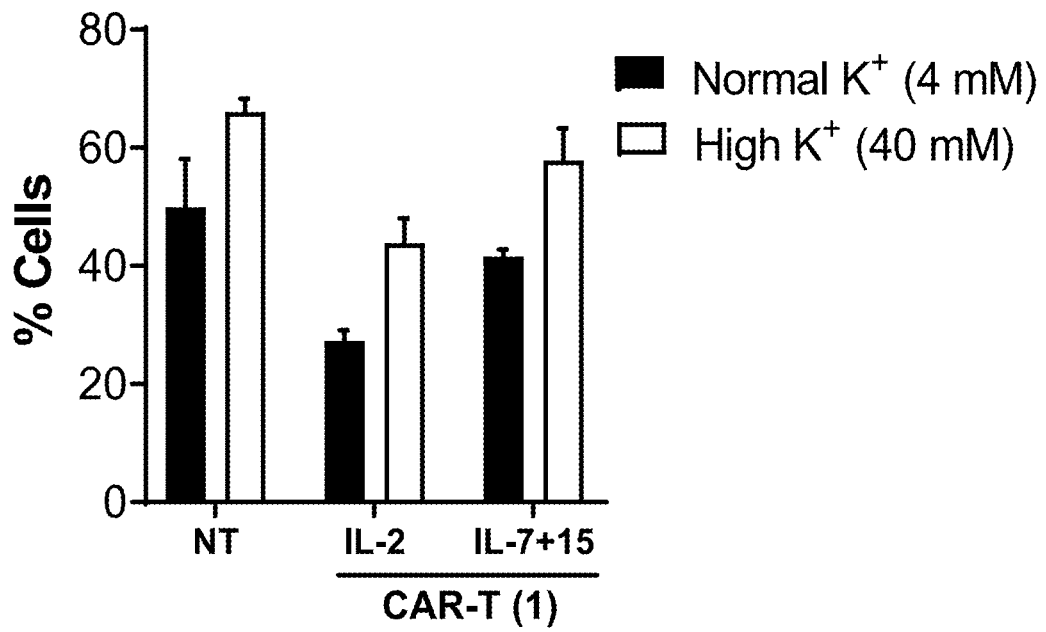
FIG. 2A depicts the effect of increased extracellular potassium (40 mM, open bars) to increase the abundance of $T_{SCM}$ cells both in IL-2- and IL-7+15 processes when compared to normal (4 mM) potassium concentrations (solid bars).
Figure 2B:
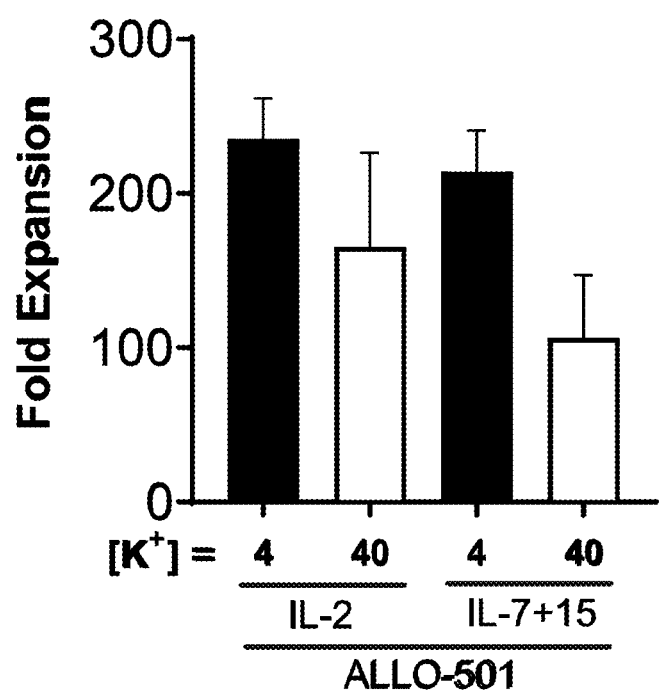
FIG. 2B depicts the effect of increased extracellular potassium (40 mM, open bars) on the expansion capacity of allogeneic CART cells both in IL-2- and IL-7+15 processes when compared to normal potassium concentrations (4 mM, solid bars).

As shown in FIG. 2A, increased extracellular potassium (40 mM, open bars) conditions increase the abundance of $T_{SCM}$ cells of allogeneic anti-CD19 CAR T cells both in IL-2- and IL-7+15 processes when compared to normal (4 mM) potassium concentrations (solid bars). In FIG. 2B, however, it was unexpectedly found that increased extracellular potassium (40 mM, open bars) conditions negatively impact the expansion capacity of allogeneic CAR T cells both in IL-2- and IL-7+15—based processes when compared to normal potassium concentrations (4 mM, solid bars).

Figure 3:
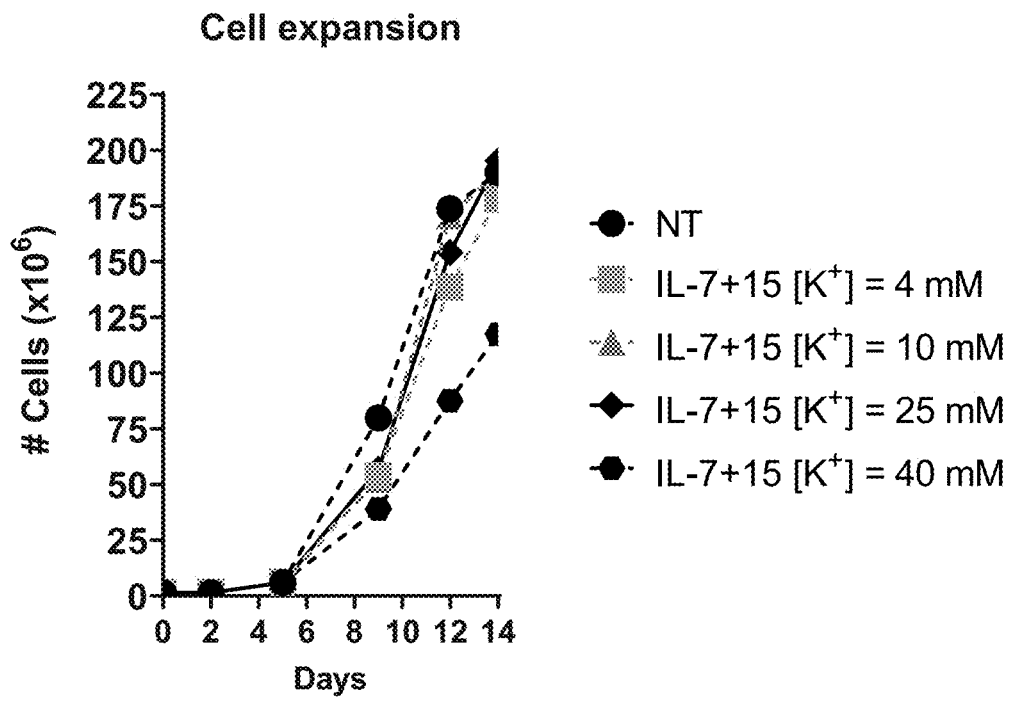
FIG. 3 depicts the effect of extracellular potassium concentrations of 25 mM and 10 mM: these concentrations did not negatively impact expansion of human T cells during allogeneic CAR T cell manufacture as compared to higher concentrations.
Figure 4:
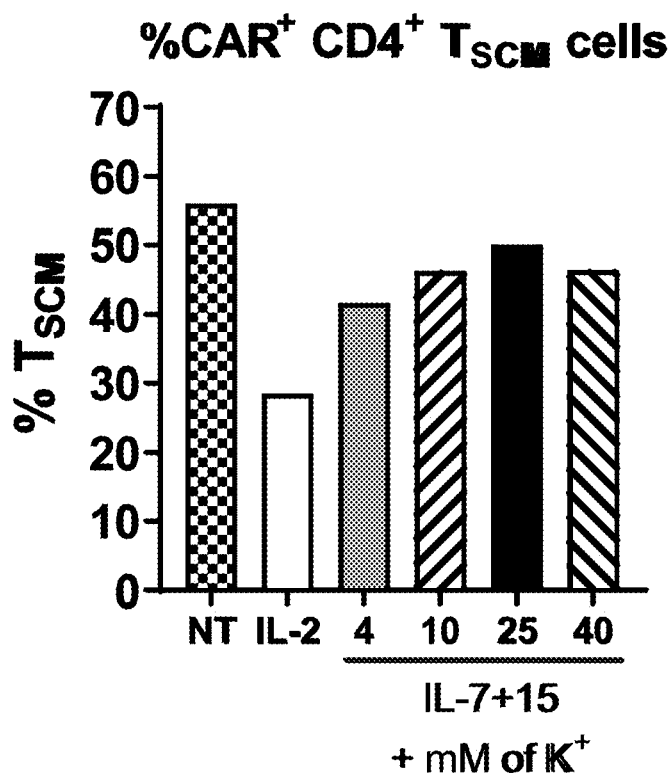
FIG. 4 depicts that maximum preservation of $T_{SCM}$ cells was achieved in 25 mM extracellular potassium.

To further enhance the benefits of high extracellular potassium during allogeneic CAR T cell manufacture, we adjusted the amount of extracellular potassium that is particularly effective for an IL-7+15-based allogeneic CAR T cell process. Extracellular potassium concentrations of 25 mM and 10 mM did not negatively impact expansion of human T cells during allogeneic CAR T cell manufacture (FIG. 3). Further, maximum preservation of $T_{SCM}$ cells was achieved in 25 mM extracellular potassium (FIG. 4).

4. Potency Studies Using Combination Supplementation with IL-7+15 and Potassium

A serial killing assay involves repeated exposure of CAR-T cells to their target causing the CAR-T cells to undergo proliferation and in certain cases, differentiation and exhaustion. This assay was used to study the potency of allogeneic CAR T cells expanded under different conditions.

Figure 5:
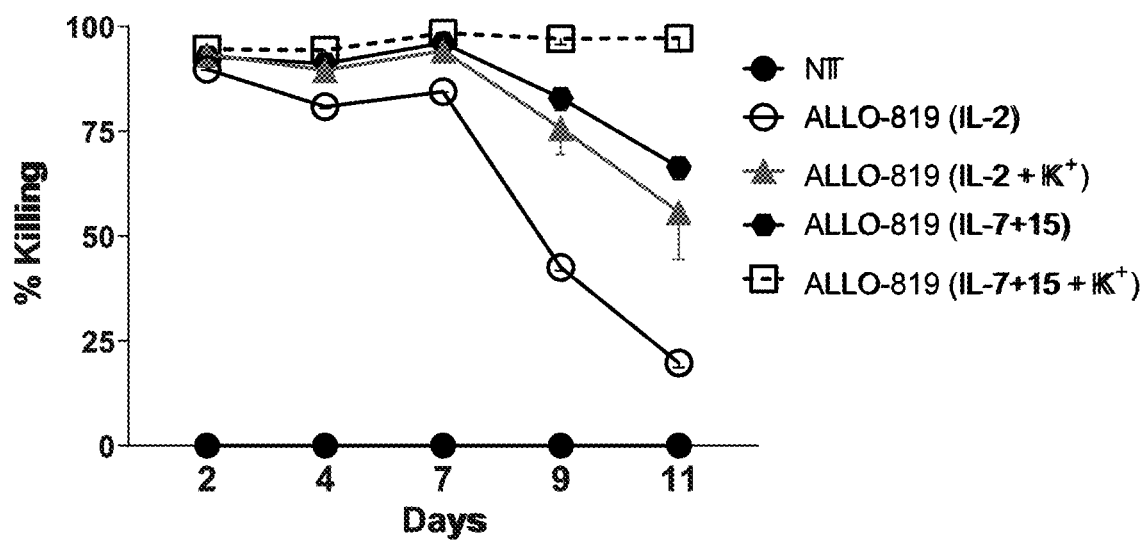
FIG. 5 shows that improved potency of Flt3-specific CAR T cells (Allo-819) was obtained using the combination of an IL-7+15-based process with 25 mM of extracellular potassium supplementation.

Having identified effective concentrations of extracellular potassium for allogeneic CAR T cell manufacture we proceeded to evaluate if a combination of IL-7+15 with a 25 mM concentration of potassium improves the potency of our allogeneic CAR T cells. Combination of an IL-7+15-based process with 25 mM of extracellular potassium supplementation leads to maximum potency of CAR T cells when compared to similar products manufacture in IL-2 with normal (4 mM) potassium concentrations (FIG. 5). Further, the combination of an IL-7+15-based process with 25 mM of extracellular potassium significantly improved potency as compared to IL-2-based process with 25 mM potassium and even further improved IL-7+15-based process with baseline level of potassium 4 mM.

In conclusion we have identified the highly effective combination of cytokines (IL-7+IL-15) and metabolic modulators (extracellular potassium), which can maximize the potency of allogeneic CAR T cells.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

SEQ ID NO. SUMMARY CHART

| SEQ ID NO. | Description | Sequence |
|---|---|---|
| 1 | Suicide polypeptide | CPYSNPSLCSGGGGSELPTQGTFSNVSTNVSPAKPTTTACP YSNPSLCSGGGGSPAPRPPTPAPTIASQPLSLRPEACRPAAG GAVHTRGLDFACDIYIWAPLAGTCGVLLLSLVITLYCNHRN RRRVCKCPRPVV |
| 2 | Suicide signal peptide | MGTSLLCWMALCLLGADHADA |
| 3 | Suicide signal peptide and suicide sequence | MGTSLLCWMALCLLGADHADACPYSNPSLCSGGGGSELPT QGTFSNVSTNVSPAKPTTTACPYSNPSLCSGGGGSPAPRPPT PAPTIASQPLSLRPEACRPAAGGAVHTRGLDFACDIYIWAP LAGTCGVLLLSLVITLYCNHRNRRRVCKCPRPVV |
| 4 | Rituximab Mimotope | CPYSNPSLC |
| 5 | Palivizumab Epitope | NSELLSLINDMPITNDQKKLMSNN |
| 6 | Cetuximab Mimotope 1 | CQFDLSTRRLKC |
| 7 | Cetuximab Mimotope 2 | CQYNLSSRALKC |
| 8 | Cetuximab Mimotope 3 | CVWQRWQKSYVC |
| 9 | Cetuximab Mimotope 4 | CMWDRFSRWYKC |
| 10 | Nivolumab Epitope 1 | SFVLNWYRMSPSNQTDKLAAFPEDR |
| 11 | Nivolumab Epitope 2 | SGTYLCGAISLAPKAQIKE |
| 12 | QBEND-10 Epitope 1 | ELPTQGTFSNVSTNVS |
| 25 Table 1 p.20 | QBEND-10 Epitope 2 | ELPTQGTFSNVSTNVSPAKPTTTA |
| 13 | Alemtuzumab Epitope | GQNDTSQTSSPS |
| 14 | FcγRIIIα hinge | GLAVSTISSFFPPGYQ |
| 15 | CD8α hinge | TTTPAPRPPTPAPTIASQPLSLRPEACRPAAGGAVHTRGLDF ACD |
| 16 | IgG1 hinge | EPKSPDKTHTCPPCPAPPVAGPSVFLFPPKPKDTLMIARTPEVTCV VDVSHEDPEVKFNWYVDGVEVHNAKTKPREEQYNSTYRVVSVL TVLHQDWLNGKEYKCKVSNKALPAPIEKTISKAKGQPREPQVYTL PPSRDELTKNQVSLTCLVKGFYPSDIAVEWESNGQPENNYKTTPPV LDSDGSFFLYSKLTVDKSRWQQGNVFSCSVMHEALHNHYTQKSL SLSPGK |
| 17 | CD8α transmembrane | IYIWAPLAGTCGVLLLSLVIT |

SEQ ID NO. SUMMARY CHART

| SEQ ID NO. | Description | Sequence |
|---|---|---|
| 18 | CD28 transmembrane domain | FWVLVVVGGVLACYSLLVTVAFIIFWV |
| 19 | CD3 zeta domain (1) | LRVKFSRSADAPAYQQGQNQLYNELNLGRREEYDVLDKR RGRDPEMGGKPRRKNPQEGLYNELQKDKMAEAYSEIGMK GERRRGKGHDGLYQGLSTATKDTYDALHMQALPPR |
| 26 | CD3 zeta domain (2) | LRVKFSRSADAPAYKQGQNQLYNELNLGRREEYDVLDKR RGRDPEMGGKPRRKNPQEGLYNELQKDKMAEAYSEIGMK GERRRGKGHDGLYQGLSTATKDTYDALHMQALPPR |
| 20 | 4-1BB | KRGRKKLLYIFKQPFMRPVQTTQEEDGCSCRFPEEEEGGCEL |
| 21 | 4-1BB nucleic acid sequence | AAGCGCGGCAGGAAGAAGCTCCTCTACATTTTTAAGCAG CCTTTTATGAGGCCCGTACAGACAACACAGGAGGAAGA TGGCTGTAGCTGCAGATTTCCCGAGGAGGAGGAAGGTG GGTGCGAGCTG |
| 22 | intracellular CD28 comprises the nucleic acid | AGATCCAAAAGAAGCCGCCTGCTCCATAGCGATTACATG AATATGACTCC ACGCCGCCCTGGCCCCACAAGGAAACACTACCAGCCTTA CGCACCACCTAGAGATTTCGCTGCCTATCGGAGC |
| 23 | CD3 zeta Intracellular domain | RSKRSRLLHSDYNINMTPRRPGPTRKHYQPYAPPRDFAAYRS |
| 24 | CD3 zeta nucleic acid sequence | AGGGTGAAGTTTTCCAGATCTGCAGATGCACCAGCGTAT CAGCAGGGCCAGAACCAACTGTATAACGAGCTCAACCT GGGACGCAGGGAAGAGTATGACGTTTTGGACAAGCGCA GAGGACGGGACCCTGAGATGGGTGGCAAACCAAGACGA AAAAACCCCCAGGAGGGTCTCTATAATGAGCTGCAGAA GGATAAGATGGCTGAAGCCTATTCTGAAATAGGCATGA AAGGAGAGCGGAGAAGGGGAAAAGGGCACGACGGTTT GTACCAGGGACTCAGCACTGCTACGAAGGATACTTATGA CGCTCTCCACATGCAAGCCCTGCCACCTAGG |

What is claimed is:

1. A method of obtaining a population of CD4+ T cells and CD8+ T cells in vitro, comprising culturing an initial population of CD4+ T cells and CD8+ T cells with a cell growth medium comprising
    a first stimulant IL-7 in a concentration of 3000 IU/mL to 5000 IU/mL and a second stimulant IL-15 in a concentration of 25 IU/mL to 50 IU/mL; and
    an extracellular modulator of cell metabolism that is extracellular potassium in a concentration of about 10 mM to about 40 mM,
    wherein the first stimulant and the second stimulant are present in a concentration ratio of about 100:1.

2. The method of claim 1, wherein the obtained population of CD4+ T cells and CD8+ T cells is enriched in TCM and/or Tscm cells.

3. The method of claim 1, wherein the obtained population of CD4+ T cells and CD8+ T cells comprises at least about 30%, 35%, 40%, or 45% Tscm cells.

4. The method of claim 3, wherein the obtained population of CD4+ T cells and CD8+ T cells comprises at least about 40% Tscm cells.

5. The method of claim 1, wherein the obtained population of CD4+ T cells and CD8+ T cells is about 100-to about 1000-fold enriched in TCM and/or Tscm than TCM and/or Tscm of the initial population of CD4+T cells and CD8+ T cells as measured over a period of about 7-16 days.

6. The method of claim 5, wherein the obtained population of CD4+ T cells and CD8+ T cells is about 100-to about 1000-fold enriched in TCM and/or Tscm than TCM and/or Tscm of the initial population of CD4+ T cells and CD8+ T cells as measured over a period of about 10-14 days.

7. The method of claim 6, wherein the obtained population of CD4+ T cells and CD8+ T cells is at least about 100-or about 200-fold enriched in TCM and/or TsCM than TCM and/or Tscm of the initial population of CD4+T cells and CD8+T cells.

8. The method of claim 1, wherein the initial population of CD4+ T cells and CD8+ T cells is a population of engineered T cells.

9. The method of claim 8, wherein the initial population of CD4+ T cells and CD8+ T cells is a population of T cells expressing one or more chimeric antigen receptors.

10. The method of claim 1, wherein the extracellular potassium is in a concentration of about 10 mM to about 30 mM.

11. The method of claim 10, wherein the extracellular potassium is present as KCl.

12. The method of claim 1, wherein the extracellular potassium is present in a concentration of about 10 mM to about 25 mM, about 20 mM to about 35 mM, or about 20 mM to about 30 mM.

13. The method of claim 1, wherein the extracellular potassium is present in a concentration of about 10 mM, about 20 mM or about 25 mM.

14. The method of claim 13, wherein the extracellular potassium is present as KCl.

15. The method of claim 1, wherein the extracellular potassium is present as KCl.

16. The method of claim 1, wherein cell culture medium comprises the first stimulant that is IL-7 in a concentration of 5000 IU/mL, and the second stimulant that is IL-15 in a concentration of 50 IU/mL.

17. The method of claim 16, wherein the extracellular potassium is present in a concentration of about 10 mM, about 20 mM or about 25 mM in the form of KCl.

18. The method of claim 1, wherein the initial population of CD4+ T cells and CD8+ T cells are isolated from peripheral blood mononuclear cells (PBMCs).

\* \* \* \* \*